US011612592B2

(12) United States Patent
Liang et al.

(10) Patent No.: US 11,612,592 B2
(45) Date of Patent: Mar. 28, 2023

(54) LIQUID FORMULATIONS CONTAINING PICOSULFATE AND MAGNESIUM CITRATE

(71) Applicant: FERRING B.V., Hoofddorp (NL)

(72) Inventors: Alfred Chi-Yeh Liang, Rahway, NJ (US); Nipul Ghanshyambhai Patel, Avenel, NJ (US); Jian-Xin Li, Edison, NJ (US)

(73) Assignee: FERRING B.V., Hoofddorp (NL)

( * ) Notice: Subject to any disclaimer, the term of this patent is extended or adjusted under 35 U.S.C. 154(b) by 1258 days.

(21) Appl. No.: 15/238,408

(22) Filed: Aug. 16, 2016

(65) Prior Publication Data

US 2017/0049758 A1 Feb. 23, 2017

Related U.S. Application Data

(60) Provisional application No. 62/205,917, filed on Aug. 17, 2015.

(51) Int. Cl.
| | | |
|---|---|---|
| *A61K 31/4402* | (2006.01) | |
| *A61K 47/02* | (2006.01) | |
| *A61K 47/12* | (2006.01) | |
| *A61K 9/08* | (2006.01) | |
| *A61K 47/36* | (2006.01) | |
| *A61K 47/38* | (2006.01) | |
| *A61K 31/194* | (2006.01) | |
| *A61K 47/16* | (2006.01) | |
| *A61K 9/00* | (2006.01) | |
| *A61K 33/08* | (2006.01) | |

(52) U.S. Cl.
CPC ........ *A61K 31/4402* (2013.01); *A61K 9/0095* (2013.01); *A61K 9/08* (2013.01); *A61K 31/194* (2013.01); *A61K 33/08* (2013.01); *A61K 47/02* (2013.01); *A61K 47/12* (2013.01); *A61K 47/16* (2013.01); *A61K 47/36* (2013.01); *A61K 47/38* (2013.01)

(58) Field of Classification Search
CPC .... A61K 31/4402; A61K 9/0095; A61K 9/08; A61K 31/194; A61K 33/08; A61K 47/02; A61K 47/12; A61K 47/16; A61K 47/36; A61K 47/38; A61P 1/10
See application file for complete search history.

(56) References Cited

U.S. PATENT DOCUMENTS

| | | |
|---|---|---|
| 5,215,769 A | 6/1993 | Fox et al. |
| 5,498,425 A | 3/1996 | Wood et al. |
| 8,450,338 B2 | 5/2013 | Xu et al. |
| 8,481,083 B2 | 7/2013 | Xu et al. |
| 9,827,231 B2 | 11/2017 | Nam |
| 10,624,879 B2 | 4/2020 | Nam et al. |
| 2013/0018223 A1 | 1/2013 | Joseph et al. |
| 2013/0149390 A1 | 6/2013 | Gorelick et al. |

| | | | |
|---|---|---|---|
| 2015/0072014 A1 * | 3/2015 | Essakimuthu | A61K 9/1617 424/490 |
| 2016/0324837 A1 * | 11/2016 | Nam | A61K 9/08 |
| 2018/0015078 A1 | 1/2018 | Liang et al. | |
| 2018/0235947 A1 | 8/2018 | Nam et al. | |

FOREIGN PATENT DOCUMENTS

| | | | |
|---|---|---|---|
| CA | 2942878 | | 9/2015 |
| EP | 401096 | A * | 12/1990 |
| IN | 1605/CHE/2006 | A | 11/2008 |
| JP | S5697248 | | 8/1981 |
| JP | H04-234960 | A | 8/1992 |
| JP | 2557111 | B | 11/1996 |
| JP | H10-327805 | A | 12/1998 |
| JP | H11-299454 | A | 11/1999 |
| JP | 2002-010765 | A | 1/2002 |
| KR | 10-1166099 | B1 | 6/2012 |
| KR | 1420315 | B1 * | 7/2014 |
| KR | 101420315 | | 7/2014 |
| KR | 2015-0016666 | A | 2/2015 |
| KR | 20150016666 | | 2/2015 |
| RU | 2342928 | C2 | 1/2009 |
| RU | 2353412 | C2 | 4/2009 |
| RU | 2473332 | C2 | 1/2013 |
| RU | 2482850 | C2 | 5/2013 |
| WO | WO-91/19692 | A2 | 12/1991 |
| WO | WO 01/66083 | | 9/2001 |
| WO | WO-01/66083 | A1 | 9/2001 |
| WO | WO-2011/078828 | A1 | 6/2011 |
| WO | WO-2011/142731 | A2 | 11/2011 |
| WO | WO-2012/102799 | A2 | 8/2012 |
| WO | WO-2014/016671 | A2 | 1/2014 |
| WO | WO-2014/032108 | A1 | 3/2014 |
| WO | WO 2015/141897 | | 9/2015 |

(Continued)

OTHER PUBLICATIONS

Sortwell et al. Bartek [online]; 1996; downloaded from <URL http://citeseerx.ist.psu.edu/viewdoc/download?doi=10.1.1.548.4424 &rep1&type=pdf > on Jun. 30, 2019; 10 pages. (Year: 1996).*
Duarte et al. Acta horticulturae. 2012; 933: 601-606. (Year: 2012).*
Rabizadeh et al. Mineralogical Magazine. 2014; 78(6): 1465-1472. (Year: 2014).*
Anonymous. Alginates. Technical Evaluation Report Compiled by the OMRI for the USDA National Organic Program. Organic Materials Review Institute [online]; 2015; published Feb. 5, 2015; downloaded from <URL https://www.ams.usda.gov/sites/default/files/media/alginates%20TR%202015.pdf > 23 pages. (Year: 2015).*
Database WPI Week 201459, Jul. 17, 2014, Thomson Scientific, London, GB; AN 2014-N77931 XP002763689,—& KR 101 420 315 K2 (Nam B G) Jul. 17, 2014, abstract.

(Continued)

*Primary Examiner* — David Browe
(74) *Attorney, Agent, or Firm* — Foley & Lardner LLP

(57) ABSTRACT

Liquid formulations containing picosulfate and magnesium citrate are provided. The compositions can include one or more precipitation inhibitors such as carboxylic acids (e.g., malonic acid), soluble anionic polymers and ammonium salts. The formulations are useful to treat constipation or for the clearance of the bowel prior to X-ray examination, endoscopy or surgery.

20 Claims, No Drawings

(56) References Cited

FOREIGN PATENT DOCUMENTS

| WO | WO-2015/141897 A1 | 9/2015 |
|---|---|---|
| WO | WO-2017/031121 A1 | 2/2017 |
| WO | WO-2018/009761 | 1/2018 |

OTHER PUBLICATIONS

Database WPI Week 201522, Feb. 13, 2015, Thomson Scientific, London, GB; AN 2015-14706W, XP002763690,—& KR 2015 0016666 KI (Hee Y L), Feb. 13, 2015, abstract.

Database WPI Week 200167, Sep. 13, 2001, Thomson Scientific, London, GB; AN 20001-596804, XP002763710, & WO 01/66083, Sep. 13, 2001.

International Search Report and Written Opinion in International Application No. PCT/US2016/047188, dated Nov. 11, 2016, 13 pages.

Anonymous., "CHEBI:114786—sodium disulfite," ChEBI [online]; updated Apr. 12, 2016; downloaded from <URL: https://www.ebi.ac.uk/chebi/searchld.do?chebild=CHEBI:114786> on Oct. 25, 2019; 4 pages (2016).

Office Action dated Oct. 30, 2019 in application No. U.S. Appl. No. 15/643,727 (US 2018-0015078).

"Guidance for Industry: Q1A(R2) Stability Testing of New Drug Substance and Products," FDA (Nov. 2003).

"Sodium Picosulfate, Magnesium Oxide, and Anhydrous Citric Acid (PREPOPIK) for Oral Solution," National Drug Monograph (Jun. 2013) Available online, URL: <https://www.pbm.va.gov/clinicalguidance/drugmonographs/PicosulfateMagnesiumOxideCitricAcidPREPOPIKMonoqraph.pdf>.

"Sodium picosulfate," Wikipedia, obtained online, URL: <https://en.wikipedia.org/wiki/Sodium_picosulfate> (downloaded May 2019).

"UKPAR, Sodium Picosulfate 5mg/5ml Oral Solution, PL 17496/0022" Medicines & Healthcare Products Regulatory Agency, (2007).

Albugeaey et al., Tu1037 How Bad Was That Bowel Prep? Results of a Patient Questionnaire Survey at a University Center, Gastrointestinal Endoscopy, 83(5 Suppl.), p. AB539 (May 2016).

Barkun et al., "Commonly Used Preparations for Colonoscopy: Efficacy, Tolerability and Safety—A Canadian Association of Gastroenterology Position Paper," Can. J. Gastroenterol., vol. 20, No. 11, pp. 699-710, (Nov. 2006).

Chakraborty et al., United States Food and Drug Administration, Center for Drug Evaluation and Research, Pharmacology Review(s) for Application No. 21-551; HalfLytely, Aug. 2012, 24 pp.

Confidential Detailed Factual and Legal Basis for Paragraph IV Certification That U.S. Pat. No. 9,827,231 Is Invalid, Unenforceable, and/or Will Not Be Infringed (Apr. 4, 2019) (Redacted).

Crowley, "Solutions, Emulsions, Suspensions, and Extracts," Remington: The Science and Practice of Pharmacy, 21st Edition, Chapter 39, pp. 745-775.

Drugs.com Prepopik—How does this stuff taste? How much do you have to drink?, https://www.drugs.com/answers/prepopik-bowel-preps-before-unable-finish-simply-58434.html (retrieved Jun. 20, 2017, 3pp) (year 2017).

Du et al., "Comparison of Bowel Preparation Quality With a Bowel Purgative Containing Sodium Picosulfate, Magnesium Oxide and Citric Acid Versus a PEG-ELS Solution: A Prospective RCT in China Using Chinese Language Validated Ottawa Scale," Gastrointestinal Endoscopy, SU1303, vol. 75, No. 4S, p. AB286, (2012).

Ducolax Pico Liquid Package Leaflet (Jun. 2013).

European Search Report in Application No. 14886464.8, dated Sep. 18, 2017, 7 pp.

Ferring Pharmaceuticals Inc., Prepopik® Highlights of Prescribing Information, Jul. 2012, 13 pp.

Handbook of Pharmaceutical Excipients Sixth Edition, Edited by RC Rowe, PJ Sheskey and ME Quinn; Pharmaceutical Press (2009) (Year: 2009).

International Search Report and Written Opinion in Internation Application No. PCT/US2016/047188, dated Nov. 11, 2016, 13 pages.

International Search Report and Written Opinion in International Application No. PCT/US2017/041047, dated Sep. 29, 2017, 16 Pages.

International Search Report in International Application No. PCT/KR2014/005512, dated Dec. 17, 2014, 13 pp.

Notice of Allowance dated Jul. 8, 2019 in U.S. Appl. No. 15/822,298 (US 2018-0235947).

Office Action dated Feb. 25, 2019 in U.S. Appl. No. 15/822,298 (US 2018-0235947).

Pdr, "Physicians' Desk Reference 2013," 67th Edition (2012), (Prepopik Prescribing Information).

Savic et al., "Monitoring of Thermal and Oxidation Stability of Sodium Picosulfate by Modified RP-HPLC Method," Chemical Industry & Chemical Engineering Quarterly 16 (1) pp. 103-110(2010).

Song et al., Effectiveness of Sodium Picosulfate/Magnesium Citrate (PICO) for Colonoscopy Preparation Ann Coloproctol 2014, 30(5), 222-227.

SUPREP Prescribing Information (Aug. 2010).

Third Party Observation dated May 28, 2019 in European Application No. 14886464.8.

Uselton et al., "Assuring Continuous Compliance with Joint Commission Standards: A Pharmacy Guide," Eighth Edition (2010).

Notice of Allowance dated Mar. 6, 2020, in U.S. Appl. No. 15/822,298 (US 2018-0235947).

Office Action dated Mar. 18, 2020, in U.S. Appl. No. 15/643,727 (US 2018-0015078).

"Malic Acid," Handbook of Pharmaceutical Excipients, Sixth Edition, Edited by RC Rowe, PJ Sheskey and ME Quinn; Pharmaceutical Press, pp. 411-413 (2009).

\* cited by examiner

LIQUID FORMULATIONS CONTAINING PICOSULFATE AND MAGNESIUM CITRATE

CROSS-REFERENCE TO RELATED APPLICATIONS

This application claims the benefit of U.S. Provisional Application No. 62/205,917, filed Aug. 17, 2015, which is hereby incorporated by reference in its entirety.

TECHNICAL FIELD

This invention relates to liquid formulations useful to treat constipation or for the clearance of the bowel prior to X-ray examination, endoscopy or surgery.

BACKGROUND

Picosulfate, used in the form of its bis-sodium salt, sodium picosulfate (I), is a stimulant laxative.

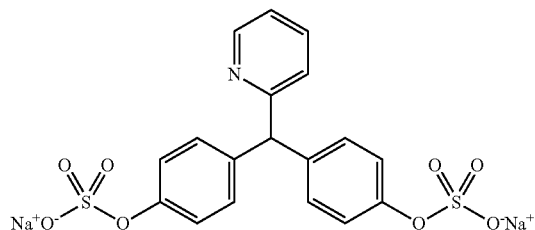

(I)

Pharmaceutical products containing picosulfate in the form of sodium picosulfate can be used to treat constipation or for the clearance of the bowel prior to X-ray examination, endoscopy or surgery. Particularly useful are products that contain sodium picosulfate in combination with magnesium oxide and anhydrous citric acid, which together in solution form magnesium citrate, an osmotic laxative with a powerful cathartic effect. Examples of such formulations are sold under the trade names PICOPREP® and PREPOPIK®. These products contain sodium picosulfate along with magnesium oxide and citric acid in the form of a solid that must be dissolved to be taken orally by the patient and provides a strong laxative that is easily palatable. The products are particularly effective to prepare patients for colonoscopy. In particular, the products include citric acid, magnesium oxide, and sodium picosulfate, as active ingredients, along with $KHCO_3$, sodium saccharin, and flavoring (e.g., orange flavor).

The existing products containing sodium picosulfate in combination with magnesium oxide and citric acid do, however, suffer from disadvantages. One is that the formulations do not dissolve immediately. For example, the patient instruction sheet for the PREPOPIK® product instructs the patient to pour the solid contents of a packet of the preparation in 5 fluid ounces (150 mL) of water in a cup, and to stir the resulting mixture for 2-3 min. before drinking the entire contents of the cup. If the patient fails to follow the procedure precisely, e.g., by failing to stir the contents for the full 2-3 min. before consumption, there is a risk that the product will not be fully dissolved and that the patient will receive less than a full dose of the product, and that the product will therefore not be as effective as intended.

To overcome the disadvantages described above, it would be desirable to be able to supply formulations containing picosulfate and magnesium citrate (MgO/citric acid) in liquid form, ready for consumption by the patient. However, dissolution of existing formulations containing sodium picosulfate and magnesium citrate leads to compositions that are unstable when stored or allowed to stand, with precipitates containing magnesium salts being formed from the solution.

WO2015/141897 discusses liquid pharmaceutical compositions containing sodium picosulfate, magnesium oxide, and citric acid. Solubilizing agents were found ineffective for preventing the formation of precipitates from the solution. Precipitation was delayed at low pH (4.1), but decomposition occurred to form the known mono-sulfate hydrolysis product Sodium Picosulfate Related Compound A ([(4-hydroxyphenyl)(pyridin-2-yl)methyl]phenyl sodium sulfate). Malic acid could be used to inhibit precipitation at pH 4.7-5.1, but other carboxylic acids were ineffective.

Recently, a liquid formulation containing sodium picosulfate and magnesium citrate (PICOSOLUTION™), has recently been made commercially available in Korea by Pharmbio Co., Ltd.

There remains a need, however, for new liquid formulations containing picosulfate and magnesium citrate.

SUMMARY

The present application provides new liquid formulations containing picosulfate and magnesium citrate that have improved stability.

The present application provides a liquid formulation that includes sodium picosulfate; magnesium citrate (MgO/citric acid); and at least one precipitation inhibitor. The precipitation inhibitor can be a carboxylic acid, and/or an ammonium salt and/or a soluble anionic polymer. The formulation can be in the form of an aqueous solution having a pH in the range from about 4.0 to about 6.5, preferably from about 4.0 to about 5.5.

In some embodiments, the precipitation inhibitor can be malonic acid or tartaric acid, preferably malonic acid, when the formulation does not comprise an ammonium salt or a soluble anionic polymer.

The liquid formulation can include sodium picosulfate at a concentration in the range from about 0.10 mM to about 0.15 mM, e.g., in the range from about 0.13 mM to about 0.15 mM or 0.12 mM to about 0.13 mM.

The liquid formulation can include magnesium citrate that comprises magnesium and citric acid in a molar ratio in the range from about 1:1 to about 1.5:1, e.g., a molar ratio of about 1.4:1. The magnesium citrate can be present at a concentration of magnesium in the range from about 0.2 to about 0.8 M, e.g., in the range from about 0.5 to about 0.6 M. The magnesium citrate can be formed from magnesium oxide and citric acid.

In some embodiments, the formulation includes a carboxylic acid. The carboxylic acid can be selected from acetic acid, arginine, ascorbic acid, asparagine, aspartic acid, citric acid, cysteine, fumaric acid, formic acid, gluconic acid, glucuronic acid, glutamic acid, glutamine, glutaric acid, glycolic acid, histidine, lactic acid, lysine, maleic acid, malic acid, malonic acid, methionine, oxalic acid, propionic acid, serine, succinic acid, tartaric acid, threonine, tryptophan, and tyrosine. In some embodiments, the carboxylic acid can be selected from acetic acid, arginine, ascorbic acid, asparagine, aspartic acid, citric acid, fumaric acid, formic acid, gluconic acid, glucuronic acid, glutaric acid, glycolic acid, histidine, lactic acid, lysine, maleic acid, malic acid, malonic acid, methionine, oxalic acid, serine, succinic acid and tartaric acid. In some embodiments, the carboxylic acid is selected from the group consisting of gluconic acid, malic acid, malonic acid, succinic acid and tartaric acid. In some embodiments, the carboxylic acid is selected from the group consisting of gluconic acid, malic acid, malonic acid, and tartaric acid. In some embodiments, the carboxylic acid is malonic acid. In some embodiments, the carboxylic acid is tartaric acid. The carboxylic acid can be present in an amount from about 0.01 M to about 5 M, e.g., about 0.1 M to about 1 M.

In some embodiments, the formulation includes a soluble anionic polymer. The soluble anionic polymer can be a polysaccharide polymer. The soluble anionic polymer can be a polysaccharide polymer that includes carboxylic acid groups. The soluble anionic polymer can be selected from the group consisting of alginic acid, carboxymethylcellulose, carrageenans, polyacrylic acid and copolymers thereof, and xanthan gum. The soluble polymer can be, e.g., sodium alginate or sodium carboxymethylcellulose. In some embodiments the soluble anionic polymer is alginic acid. In some embodiments the soluble anionic polymer is carboxymethylcellulose. In some embodiments the soluble anionic polymer is a carrageenan. In some embodiments the soluble anionic polymer is xanthan gum. The soluble anionic polymer can be present in an amount from about 0.5 g/L to about 25 g/L. In some embodiments, the soluble anionic polymer can be present in an amount from about 5 g/L to about 20 g/L. In some embodiments, the soluble anionic polymer can be present in an amount from about 1 g/L to about 10 g/L.

In some embodiments, the formulation includes an ammonium salt. The ammonium salt can be selected from ammonium acetate, ammonium chloride, and ammonium sulfate. The ammonium salt can be present in an amount from about 1 g/L to about 40 g/L.

The pH of the liquid formulation can be in the range from about 4.0 to about 6.5, preferably from about 4.0 to about 5.5, or from about 4.5 to about 5.2, more preferably in the range from about 4.7 to about 4.9. The pH can be about 4.8.

The liquid formulation can be is stable for at least 10 days, preferably for at least 60 days, or more preferably for at least 1 year, or at least about 2 years, when stored at a temperature of about 20° C. to 25° C. (e.g., about 20° C.).

The present disclosure further provides a pharmaceutical composition that includes:
 sodium picosulfate;
 magnesium oxide;
 citric acid; and
 at least one precipitation inhibitor, wherein the precipitation inhibitor is a carboxylic acid, an ammonium salt or a soluble anionic polymer.

In some embodiments, the precipitation inhibitor is malonic acid or tartaric acid if the composition does not comprise an ammonium salt or a soluble anionic polymer.

The present disclosure further provides a method of preparing a liquid formulation comprising dissolving ingredients comprising sodium picosulfate, magnesium oxide, citric acid and at least one precipitation inhibitor selected from a carboxylic acid, an ammonium salt and a soluble anionic polymer to form a liquid formulation, wherein the precipitation inhibitor is malonic acid or tartaric acid if the liquid formulation does not comprise an ammonium salt or a soluble anionic polymer. The method can include dissolving the ingredients in water. The method can also include adjusting the pH of the liquid formulation to a pH in the range from about 4.0 to about 6.5, from about 4.0 to about 5.5, or from about 4.7 to about 4.9, preferably a pH of about 4.8. A liquid formulation prepared by such a method is provided.

The disclosure also provide a method of clearing the bowel of a subject in need thereof, comprising administering to the subject an effective amount of a liquid formulation as described herein. Clearing of the bowel can be performed to prepare the subject prior to X-ray examination, endoscopy, or surgery.

Also provided herein is a method for determining the stability of a liquid formulation comprising sodium picosulfate and magnesium citrate. The method includes: (a) freezing the liquid formulation to provide a frozen formulation; (b) thawing the frozen liquid to provide a thawed formulation; (c) observing the thawed formulation to determine the absence or presence of a precipitate in the thawed formulation; and (d) determining, based on the absence of a precipitate in the thawed formulation, that the liquid formulation is stable, or determining, based on the presence of a precipitate in the thawed formulation, that the liquid formulation is unstable. Steps (a) and (b) can be repeated sequentially one or more additional time (e.g., a total of five times).

Although methods and materials similar or equivalent to those described herein can be used in the practice or testing of the present invention, suitable methods and materials are described below. All publications, patent applications, patents, and other references mentioned herein are incorporated by reference in their entirety. Where the first page number of a reference is given in a citation, it is to be understood that reference is being made to the entire article cited. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Definitions

Unless defined otherwise, all technical and scientific terms used herein have the same meaning as is commonly understood by one of ordinary skill in the art to which this disclosure belongs.

For the terms "e.g." and "such as," and grammatical equivalents thereof, the phrase "and without limitation" is understood to follow unless explicitly stated otherwise.

As used herein, the singular forms "a," "an," and "the" include plural referents unless the context clearly dictates otherwise.

As used herein, the term "about" means "approximately" (e.g., plus or minus approximately 10% of the indicated value).

The term "alkali metal" refers to a metal of group 1 (group IA) of the periodic table, including lithium, sodium, potassium and cesium.

The term "carboxylic acid" refers to an organic compound that contains one of more carboxylic acid groups (—C(=O) OH). The term includes carboxylic acids in neutral (protonated) form, as well as carboxylic acids in salt (anionic or deprotonated) form.

The term "magnesium citrate" refers to a magnesium salt of citric acid. The magnesium citrate can be formed by the reaction of a magnesium base such as magnesium hydroxide, magnesium oxide or magnesium carbonate with citric acid, e.g., anhydrous citric acid or citric acid monohydrate.

The term "soluble" describes a compound that dissolves in water or an aqueous solution. Compounds described as "soluble" used in the formulations described herein have a solubility that permits at least the amount of the compound included in the formulation to be dissolved.

The term "soluble anionic polymer" refers to a soluble polymer that contains acidic functional groups and that is therefore anionic at neutral pH (i.e., a pH of about 7) or at basic pH (i.e., a pH of greater than 7). A soluble anionic polymer can also be anionic at moderately acidic pH (e.g., a pH in the range from about 3 to about 7).

The term "stable" when used to refer to liquid formulations as described herein refers to the absence of change in the formulation over a given period of time (during which the formulation is considered to be "stable.") Specifically, the term refers to the absence of visible precipitation occurring from the formulation or decomposition of the formulation. Stability is indicated by the absence of visible precipitates and the presence of a substantial proportion, e.g., at least 90%, preferably at least about 95%, and more preferably at least about 98% or at least about 99%, of the picosulfate originally present in the solution, that is chemically unchanged (e.g., as determined by HPLC). The composition may form less than 10%, preferably less than about 5%, and more preferably less than about 2% or less than about 1% of related substances (e.g., as determined by HPLC), and may, in particular, form less than 10%, preferably less than about 5%, and more preferably less than about 2% or less than about 1% of Sodium Picosulfate Related Compound A ([(4-hydroxyphenyl)(pyridin-2-yl)methyl] phenyl sodium sulfate). The period of time during which the formulation is stable can be at least about thirty days, about sixty days, about 90 days, preferably at least about six months, more preferably at least about a year, or more preferably, at least about two years. The storage can be, e.g., under refrigeration conditions (e.g., about 4° C.), or under ambient conditions, (e.g., about 20° C. or about 25° C., or in the range from about 20° C. to about 25° C.).

At various places in the present specification, certain features are disclosed in groups or in ranges. It is specifically intended that such a disclosure include each and every individual sub-combination of the members of such groups and ranges. For example, the term "$C_{1-6}$ alkyl" is specifically intended to individually disclose (without limitation) methyl, ethyl, $C_3$ alkyl, $C_4$ alkyl, $C_5$ alkyl and $C_6$ alkyl.

Abbreviations

The following abbreviations and symbols may be used in the present disclosure: aq. (aqueous); ° C. (degrees Celsius); d (day(s)); EDTA (ethylenediaminetetraacetic acid); Ex. (example); g (gram(s)); h (hour(s)); HCl (hydrochloric acid); HPMC (hydroxypropylmethylcellulose); HPLC (high-performance liquid chromatography); $KHCO_3$ (potassium bicarbonate); L (liter(s)); M (molar); mg (milligram(s)); mL (milliliter); mm (millimeter(s)); mmol (millimole(s)); mM (millimolar); μm (micrometer(s); PTFE (polytetrafluoroethylene); ppt (precipitate/precipitation); NaOH (NaOH); Na-saccharin (sodium saccharin); Na-CMC (sodium carboxymethylcellulose); Ref (reference). Other common abbreviations may also be used herein.

Compositions

The present disclosure provides stable liquid formulations (compositions) comprising picosulfate and magnesium. The formulations are stable upon storage and are useful to treat constipation or for the clearance of the bowel prior to X-ray examination, endoscopy or surgery.

The formulations include a picosulfate salt, a magnesium salt, and one or more of a carboxylic acid, an ammonium salt or a soluble anionic polymer in an aqueous solution.

The picosulfate salt can be an alkali metal picosulfate, e.g., sodium picosulfate. Preferably, the picosulfate salt is sodium picosulfate. The picosulfate can be present in the composition at a concentration in the range from about 0.10 mM to about 0.15 mM, e.g., about 0.11 mM to about 0.15 mM, about 0.12 mM to about 0.15 mM, about 0.13 mM to about 0.15 mM, about 0.14 mM to about 0.15 mM, about 0.11 mM to about 0.14 mM, 0.12 mM to about 0.14 mM, 0.13 mM to about 0.14 mM, 0.11 mM to about 0.13 mM, 0.12 mM to about 0.13 mM, or about 0.11 mM to about 0.13 mM. Preferred concentrations are in the range from about 0.12 mM to about 0.14 mM, or from about 0.13 mM to about 0.15 mM, preferably about 0.13 mM or about 0.14 mM. The picosulfate salt can be present in an amount that provides a dose of sodium picosulfate, or a dose equivalent to a dose of sodium picosulfate, wherein the amount of sodium picosulfate in the dose is from about 5 mg to about 10 mg, preferably from about 8 mg to about 12 mg, about 9 mg to about 11 mg, or about 10 mg, preferably a 10 mg dose of sodium picosulfate. The dose can be included in a volume in the range from about 50 mL to about 250 mL, e.g., from about 100 mL to about 200 mL, from about 150 mL to about 170 mL; e.g., about 100 mL, about 120 mL, about 125 mL, about 140 mL, about 150 mL, about 160 mL, about 175 mL, about 180 mL, or about 200 mL.

The magnesium salt can be magnesium citrate. The magnesium citrate can be formed by the reaction of a magnesium base, e.g., magnesium hydroxide, magnesium oxide or magnesium carbonate, preferably magnesium oxide, with citric acid, e.g., anhydrous citric acid or citric acid monohydrate, preferably anhydrous citric acid. The magnesium citrate can include salts in which the magnesium and citrate components are present in a molar ratio in the range from about 1:1 to about 1.5:1, e.g., from about 1.1:1 to about 1.5:1, about 1.2:1 to about 1.5:1, about 1.3:1 to about 1.5:1, about 1.4:1 to about 1.5:1, about 1:1 to about 1.4:1, about 1.2:1 to about 1.4:1, about 1.3:1 to about 1.4:1, about 1:1 to about 1.3:1, about 1.1:1 to about 1.3:1, about 1.2:1 to about 1.3:1, or about 1:1 to about 1.2:1. The magnesium and citric acid components can also be present in a molar ratio in the range from about 0.5:1 to about 1:1, 0.6:1 to about 1:1, 0.7:1 to about 1:1, 0.8:1 to about 1:1, or about 0.9:1 to about 1:1. 16. Preferably, the magnesium and citrate components can be present in a molar ratio of about 1.4:1.

The magnesium salt, e.g., magnesium citrate, can be present in the formulation at a concentration that provides a concentration of magnesium in the range from about 0.1 M to about 1.0 M, e.g., from about 0.2 M to about 0.8 M, or from about 0.5 M to about 0.6 M, e.g., about 0.1 M, about 0.2 M, about 0.3 M, about 0.4 M, about 0.5 M, about 0.6 M, about 0.7 M, about 0.8 M, about 0.9 M, or about 1.0 M. Preferably, the magnesium salt is present at a concentration that provides a concentration of magnesium in the range from about 0.5 M to about 0.6 M, or at a concentration of about 0.6 M.

The magnesium salt can be present in an amount per dose that is provided, or an amount that is equivalent to the amount that is provided, when the magnesium salt is prepared from magnesium oxide and the amount of magnesium oxide is in the range from about 1 g to about 6 g, e.g., from about 2 g to about 5 g, from about 2 g to about 4 g, from about 3 g to about 5 g, or from about 3 g to about 4 g, e.g., about 1 g, about 1.5 g, about 2 g, about 2.5 g, about 3 g, about 3.5 g, about 4 g, about 4.5 g, about 5 g, about 5.5 g, or about 6 g. Preferably the magnesium salt is present in an amount per dose that is provided, or an amount that is equivalent to the amount that is provided, when the magnesium salt is prepared from magnesium oxide and the amount of magnesium oxide is about 3.5 g.

The magnesium salt can be present in an amount per dose that is provided by magnesium citrate when the magnesium citrate is prepared from magnesium oxide in the amounts specified above (or another magnesium base that provides magnesium in an equivalent amount to the amounts specified above) and citric acid. The amount of citric acid per dose can be an amount of citric acid as specified by the molar ratios above. The amount of citric acid per dose can be an amount that is provided by an amount of anhydrous citric acid (or an equivalent amount of hydrated citric acid) in the range from about 3 g to about 20 g, e.g., from about 5 g to about 15 g, from about 10 g to about 15 g, or about 9 g, about 10 g, about 11 g, about 12 g, about 13 g, about 14 g, or about 15 g, preferably about 12 g.

While not being limited by any theory, it is considered that the carboxylic acid, and/or ammonium salt and/or soluble anionic polymer in an aqueous solution help to stabilize the formulation and inhibit, retard, or prevent the precipitation of salts from the formulation. One or more of a carboxylic acid, and/or ammonium salt and/or a soluble anionic polymer can be present in the formulation. The formulation can include, e.g., a carboxylic acid and an ammonium salt (including an ammonium salt of a carboxylic acid), a carboxylic acid and a soluble anionic polymer, an ammonium salt and a soluble anionic polymer, or a carboxylic acid, an ammonium salt and a soluble anionic polymer. The formulations can also include more than one (e.g., two) of the carboxylic acid, the ammonium salt, and/or the soluble anionic polymer, including in combination with carboxylic acid(s), ammonium salt(s) and/or soluble anionic polymer(s). When used in such combinations, the carboxylic acid(s), ammonium salt(s) and/or soluble anionic polymer(s) can be any one or any two or more of the carboxylic acids, ammonium salts and/or soluble anionic polymer described herein, and, when used in combination, they can be used in the same amount specified for each component elsewhere in the present disclosure. When used in combination, the carboxylic acids, ammonium salts and/or soluble anionic polymer described herein may also be used in a smaller amount than when used individually, and may be used, e.g., in about 25%, 50% or 75% of the amount specified for each individual component elsewhere in the present disclosure.

The carboxylic acids that can be used in the formulations include water soluble carboxylic acids, which are preferred. Suitable carboxylic acids include mono-, di- and tri-carboxylic acids. Suitable carboxylic acids include $C_{1-6}$ (or $C_{1-4}$ or $C_{1-3}$) alkanoic acids, including formic, acetic and propionic acid. Suitable carboxylic acids include $C_{1-6}$ (or $C_{1-4}$ or $C_{1-3}$) alkandioic or alkenedioic acids, including oxalic acid, malonic acid, succinic acid, glutaric acid, adipic acid, fumaric acid, and maleic acid. Suitable carboxylic acids further include hydroxy-substituted acids, including mono-, di- or tri-hydroxy-substituted mono-, di- or tricarboxylic acids, including glycolic acid, malic acid, lactic acid, citric acid, tartaric acid, 3-hydroxypropionic acid, and glyceric acid. Suitable carboxylic acids further include amino-substituted acids, including α- and β-aminoacids, including glycine, arginine, histidine, lysine, aspartic acid, glutamic acid, serine, threonine, asparagine, glutamine, cysteine, methionine, proline, alanine, valine, isoleucine, leucine, phenylalanine, tyrosine, tryptophan, β-alanine, and homoserine. For acids containing one or more chiral centers, the configuration of each chiral center can be (R) or (S), and can be employed as a single isomer or mixture of isomers (e.g., a racemic mixture). For example, any of the a-amino acids arginine, histidine, lysine, aspartic acid, glutamic acid, serine, threonine, asparagine, glutamine, cysteine, methionine, proline, alanine, valine, isoleucine, leucine, phenylalanine, tyrosine, tryptophan or homoserine can be in D- or L-configuration (or as mixtures). The hydroxy-substituted carboxylic acids can also be employed in the form of stereoisomers or mixtures thereof, e.g., glycolic acid, malic acid, lactic acid, citric acid, tartaric acid, 3-hydroxypropionic acid, and glyceric acid.

Examples of suitable carboxylic acids include acetic acid, arginine, ascorbic acid, asparagine, aspartic acid, cysteine, fumaric acid, formic acid, gluconic acid, glucuronic acid, glutamic acid, glutaric acid, glycolic acid, histidine, lactic acid, lysine, maleic acid, malic acid, malonic acid, methionine, oxalic acid, propionic acid, serine, succinic acid, tartaric acid, threonine, and tyrosine. Preferred carboxylic acids are those that are approved by the Food and Drug Administration for use as inactive ingredients in pharmaceutical products. Also preferred are carboxylic acids that are approved or recognized as safe for use in food products.

When the carboxylic acid is citric acid, the citric acid can be an excess over the citric acid used to form the magnesium citrate. The carboxylic acid can be a carboxylic acid other than citric acid. The carboxylic acid can also be a carboxylic acid other than any of the other acids identified above, e.g., an acid other than malic acid. The carboxylic acid can be a carboxylic acid other than any of the following acids: acetic acid, aspartic acid, citric acid, fumaric acid, glutamic acid, lactic acid, maleic acid, malic acid, and succinic acid.

In some embodiments, the precipitation inhibitor can be malic acid.

In some embodiments, the precipitation inhibitor can be malonic acid.

In some embodiments, the precipitation inhibitor can be tartaric acid. In some embodiments, the precipitation inhibitor can be D-tartaric acid. In some embodiments, the precipitation inhibitor can be L-tartaric acid. In some embodiments, the precipitation inhibitor can be DL-tartaric acid. In some embodiments, the precipitation inhibitor can be meso-tartaric acid.

In some embodiments, the precipitation inhibitor can be malonic acid or tartaric acid when the formulation does not comprise an ammonium salt or a soluble anionic polymer.

In some embodiments, the precipitation inhibitor can be gluconic acid (e.g., as sodium gluconate).

In some embodiments, the precipitation inhibitor can be succinic acid.

The carboxylic acid can be included in the formulation in the form of a free acid, a salt, or a mixture of the acid one or more salts of the carboxylic acid, such as carboxylate salts. Examples of suitable salts include ammonium salts and alkali metal salts, e.g., sodium or potassium carboxylate salts. Sodium salts are preferred as are potassium salts. Ammonium salts are also preferred. When the acid is an amino acid, the carboxylic acid can also be used in the form of an acid addition salt, e.g., a hydrochloride salt, hydrogen sulfate salt, or a sulfate salt.

When the carboxylic acid is included in the formulation in the form of a salt, e.g., a carboxylate salt, a mineral acid can also be included in the formulation. The mineral acid can react with a carboxylate salt to form the free acid. Suitable mineral acids for this purpose include hydrochloric acid and sulfuric acid.

The amount of carboxylic acid included in the formulation can be any amount that is effective to stabilize the formulation. Limits on the amount of carboxylic acid to be included in the formulation can include limits imposed by the solubility of the carboxylic acid, by the palatability of the carboxylic acid, or the toxicity or other undesirable properties of certain carboxylic acids. The carboxylic acids can be present in the formulation at a concentration in the range from about 0.01 M to 5 M, e.g., concentrations from about 0.01 g/L to about 5 M, e.g., from about 0.01 M to about 3 M, from about 0.01 M to about 1 M, from about 0.05 M to about 5 M, from about 0.05 M to about 3 M, from about 0.05 M to about 1 M, from about 0.1 M to about 5 M, from about 0.1 M to about 3 M, or from about 0.1 M to about 1 M, e.g., about 0.1 M, about 0.2 M, about 0.3 M, about 0.4 M, about 0.5 M, about 0.6 M, about 0.7 M, about 0.8 M, about 0.9 M, about 1.0 M, about 1.2 M, about 1.4 M, about 1.5 M, about 2 M, about 3 M, about 4 M, or about 5 M. Suitable amounts of the carboxylic acids included in the formulations can include amounts in the range from about 1 g/L to about 500 g/L, e.g., from about 1 g/L to about 300 g/L, from about 1 g/L to about 100 g/L, from about 5 g/L to about 500 g/L, from about 5 g/L to about 300 g/L, from about 5 g/L to about 100 g/L, from about 10 g/L to about 500 g/L, from about 10 g/L to about 300 g/L, or from about 10 g/L to about 100 g/L. For carboxylic acids that are liquids, suitable amounts of the carboxylic acids can include amounts in the range from about 1 mL/L to about 500 mL/L, e.g., from about 1 mL/L to about 300 mL/L, from about 1 mL/L to about 100 mL/L, from about 5 mL/L to about 500 mL/L, from about 5 mL/L to about 300 mL/L, from about 5 mL/L to about 100 mL/L, from about 10 mL/L to about 500 mL/L, from about 10 mL/L to about 300 mL/L, or from about 10 mL/L to about 100 mL/L.

The soluble anionic polymer that can be used in the formulations include water soluble polymers containing carboxylic acid, sulfonic acid and sulfate groups. Water soluble polymers containing carboxylic acid groups are preferred. In some embodiments, the soluble anionic polymer is a polysaccharide polymer. Examples of suitable anionic polymers include alginic acid, carboxymethylcellulose, carrageenans, polyacrylic acid and copolymers thereof, and xanthan gum. The soluble anionic polymer can be included in the formulation in the form an acid, a salt form, in which the acidic functional groups have been deprotonated to anionic (or salt) form, or as a form in which the acidic functional groups have been partially deprotonated. The soluble anionic polymers can be, e.g., sodium alginate or sodium carboxymethylcellulose. Typically, the polymer is included in anionic form. Suitable counterions for the soluble anionic polymer include alkali metal counterions, e.g., sodium or potassium, or ammonium counterions. The sodium salt forms of the soluble anionic polymer are preferred as are the potassium salt forms.

In some embodiments, the soluble anionic polymer can be alginic acid, e.g., as sodium alginate. Examples include PROTANAL® CR 8133, PROTANAL® 8233, PROTANAL® LFR 5/60 or PROTACID® 120 NM.

In some embodiments, the soluble anionic polymer can be carboxymethylcellulose, e.g., as sodium carboxymethylcellulose. Examples include AQUALON® CMC-7L2P, or AQUALON® CMC-7LF.

In some embodiments, the soluble anionic polymer can be carrageenan, e.g., lambda-carrageenan. Examples include VISCARIN® GP 109F.

In some embodiments, the soluble anionic polymer can be poly(acrylic) acid.

In some embodiments, the soluble anionic polymer can be xanthan gum. Examples include XANTURAL® 75.

The amount of the soluble anionic polymer included in the formulation can be any amount that is effective to stabilize the formulation. Limits on the amount of the soluble anionic polymer to be included in the formulation can include limits imposed by the solubility of the soluble anionic polymer, by the palatability of the soluble anionic polymer, or the toxicity or other undesirable properties of certain soluble anionic polymer. The presence of a soluble anionic polymer can also increase the viscosity of the liquid formulation, which can also impose limits on the amount of soluble anionic polymer included in the formulation. The liquid formulation should preferably be relatively free flowing so that it can be easily consumed orally by a patient.

Suitable amounts of the soluble anionic polymer included in the formulations can include amounts in the range from about 0.5 g/L to about 25 g/L, e.g., from about 0.5 g/L to about 20 g/L, from about 0.5 g/L to about 10 g/L, from about 0.5 g/L to about 5 g/L, from about 1 g/L to about 25 g/L, from about 1 g/L to about 20 g/L, from about 1 g/L to about 10 g/L, from about 1 g/L to about 5 g/L, from about 2 g/L to about 25 g/L, from about 2 g/L to about 20 g/L, from about 2 g/L to about 10 g/L, from about 2 g/L to about 5 g/L, from about 5 g/L to about 25 g/L, from about 5 g/L to about 20 g/L, from about 5 g/L to about 10 g/L, from about 10 g/L to about 25 g/L, from about 10 g/L to about 20 g/L, from about 10 g/L to about 15 g/L, or from about 15 g/L to about 20 g/L.

In some embodiments, the formulations can include both a carboxylic acid and a soluble anionic polymer as precipitation inhibitors.

In some embodiments, the formulations can include both malic acid and alginic acid, e.g., as sodium alginate. In some embodiments, the formulations can include both malic acid and carboxymethylcellulose, e.g., as sodium carboxymethylcellulose. In some embodiments, the formulations can include both malic acid and carrageenan, e.g., lambda-carrageenan. In some embodiments, the formulations can include both malic acid and poly(acrylic) acid. In some embodiments, the formulations can include both malic acid and xanthan gum. The malic acid can be, e.g., D-, L- or DL-malic acid.

In some embodiments, the formulations can include both malonic acid and alginic acid, e.g., as sodium alginate. In some embodiments, the formulations can include both malonic acid and carboxymethylcellulose, e.g., as sodium carboxymethylcellulose. In some embodiments, the formulations can include both malonic acid and carrageenan, e.g., lambda-carrageenan. In some embodiments, the formulations can include both malonic acid and poly(acrylic) acid. In some embodiments, the formulations can include both malonic acid and xanthan gum.

In some embodiments, the formulations can include both tartaric acid and alginic acid, e.g., as sodium alginate. In some embodiments, the formulations can include both tartaric acid and carboxymethylcellulose, e.g., as sodium carboxymethylcellulose. In some embodiments, the formulations can include both tartaric acid and carrageenan, e.g., lambda-carrageenan. In some embodiments, the formulations can include both tartaric acid and poly(acrylic) acid. In some embodiments, the formulations can include both tartaric acid and xanthan gum. The tartaric acid can be, e.g., D-, L-, DL- or meso-tartaric acid.

In some embodiments, the formulations can include both gluconic acid, e.g., as sodium gluconate, and alginic acid, e.g., as sodium alginate. In some embodiments, the formulations can include both gluconic acid e.g., as sodium gluconate, and carboxymethylcellulose, e.g., as sodium carboxymethylcellulose. In some embodiments, the formulations can include both gluconic acid e.g., as sodium gluconate, and carrageenan, e.g., lambda-carrageenan. In some embodiments, the formulations can include both gluconic acid e.g., as sodium gluconate, and poly(acrylic) acid. In some embodiments, the formulations can include both gluconic acid e.g., as sodium gluconate, and xanthan gum.

In some embodiments, the formulations can include both succinic acid and alginic acid, e.g., as sodium alginate. In some embodiments, the formulations can include both succinic acid and carboxymethylcellulose, e.g., as sodium carboxymethylcellulose. In some embodiments, the formulations can include both succinic acid and carrageenan, e.g., lambda-carrageenan. In some embodiments, the formulations can include both succinic acid and poly(acrylic) acid. In some embodiments, the formulations can include both succinic acid and xanthan gum.

The ammonium salts that can be used in the formulations include water soluble salts of mineral acids or carboxylic acids. The ammonium salts that can be used in the formulation include ammonium chloride (which is preferred), ammonium hydrogen sulfate, or ammonium sulfate. The ammonium salts that can be used in the formulation also include ammonium carboxylate salts with any of the carboxylic acids identified above, e.g., ammonium formate, ammonium acetate, and ammonium propionate. The ammonium salts that can be used in the formulation can be formed in situ by the reaction of ammonia with a suitable acid.

The amount of ammonium salt included in the formulation can be any amount that is effective to stabilize the formulation. Limits on the amount of ammonium salt to be included in the formulation can include limits imposed by the solubility of the ammonium salt, by the palatability of the ammonium salt, or the toxicity or other undesirable properties of certain ammonium salts.

Suitable amounts of the ammonium salts included in the formulations can include amounts in the range from about 1 g/L to about 40 g/L, e.g., from about 1 g/L to about 20 g/L, from about 1 g/L to about 10 g/L, from about 1 g/L to about 5 g/L, from about 5 g/L to about 40 g/L, from about 5 g/L to about 20 g/L, from about 10 g/L to about 40 g/L, or from about 10 g/L to about 20 g/L.

The pH of the solution can be in the range from about 4.0 to about 6.5, preferably from about 4.0 to about 5.5. While not being limited by any theory, it is considered that a low pH (below about 6.5, or preferably below about 5.5) can be beneficial to help to stabilize the formulation and inhibit, retard, or prevent the precipitation of salts (e.g., magnesium salts) from the formulation; however, it is also understood that picosulfate can be unstable at a pH lower than about 4.0, and thus it is considered desirable that the pH of the formulation be in the range from about 4.0 to about 6.5, or, preferably, from about 4.0 to about 5.5. The pH can be in a range, e.g., from about 4.0 to about 5.2, from about 4.0 to about 5.0, from about 4.0 to about 4.8, from about 4.0 to about 4.6, from about 4.0 to about 4.5, from about 4.0 to about 4.4, from about 4.0 to about 4.2, from about 4.2 to about 5.5, from about 4.2 to about 5.2, from about 4.2 to about 5.0, from about 4.2 to about 4.8, from about 4.2 to about 4.6, from about 4.2 to about 4.5, from about 4.2 to about 4.4, from about 4.4 to about 5.5, from about 4.4 to about 5.2, from about 4.4 to about 5.0, from about 4.4 to about 4.8, from about 4.4 to about 4.6, from about 4.5 to about 5.5, from about 4.5 to about 5.2, from about 4.5 to about 5.0, from about 4.5 to about 4.8, from about 4.6 to about 5.5, from about 4.6 to about 5.2, from about 4.6 to about 5.0, from about 4.6 to about 4.8, from about 4.8 to about 5.5, from about 4.8 to about 5.2, or from about 4.8 to about 5.0. A pH in the range from about 4.5 to about 5.2 is preferred. The pH can be, e.g., about 4.0, about 4.1, about 4.2, about 4.2, about 4.3, about 4.4, about 4.5, about 4.6, about 4.7, about 4.8, about 4.9, about 5.0, about 5.1, about 5.2, about 5.3, about 5.4, or 5.5. The pH is preferably about 4.8.

To obtain the formulation to the required pH, one or more acids or bases can be included in the formulation to adjust the pH. To lower the pH, one or more acids can be used, e.g., hydrochloric acid, sulfuric acid, a carboxylic acid (which can be one or more of the carboxylic acids described in greater detail above) or an ammonium salt (which can be one or more of the ammonium salts described in greater detail above). To increase the pH, one or more bases can be used, e.g., sodium hydroxide, potassium hydroxide, sodium bicarbonate, $KHCO_3$, sodium carbonate, potassium carbonate, or sodium or potassium salts of carboxylic acids (which can be one or more of the carboxylic acids described in greater detail above). Upon reaction with other acidic or basic components of the formulation, such acids and bases can form salts that can be present as additional components of the formulation, e.g., sodium chloride, sodium sulfate, potassium sulfate, and potassium chloride.

The formulations are aqueous formulations containing water a solvent. Additional water-soluble or water-miscible solvents can also be present in the formulation, including, e.g., alcohols, including $C_{2-4}$ alcohols such as ethanol, or glycols such as polyethylene glycol.

Additional ingredients that may be present in the formulation include sweetening and flavoring agents. Examples of sweetening agent is aspartame and saccharin sodium. Examples of flavoring agents include orange flavor containing acacia gum, lactose, ascorbic acid and butylated hydroxyanisole, and cranberry flavor containing maltodextrin, glyceryl triacetate (triacetin) and sodium octenyl succinated starch.

It will be appreciated that the sodium picosulfate, magnesium salts, carboxylic acids, ammonium salts and soluble anionic polymers, and other formulation components defined above are independent components of the composition and therefore any of the identified magnesium salts, carboxylic acids, ammonium salts and soluble anionic polymers, and other formulation components can be included in the formulation. Further, each of the sodium picosulfate, magnesium salts, carboxylic acids, ammonium salts and soluble anionic polymers, and other formulation components can be included in the amounts described above.

Manufacture of the Formulation

The liquid formulation described herein can be prepared by dissolving the ingredients of the formulation in a suitable liquid, such as water, to provide any of the liquid formulations as described above. Typically, magnesium oxide and citric acid are used to provide the magnesium citrate. The ingredients are used in amounts such that, the appropriate concentrations (such as those described above) are provided when the ingredients are dissolved in a given volume (e.g., 150 mL is typically used to provide a single unit dose) of the liquid.

The present disclosure thus provides a method of preparing a liquid formulation comprising dissolving ingredients comprising sodium picosulfate, magnesium oxide, citric acid and at least one precipitation inhibitor selected from a carboxylic acid, an ammonium salt and a soluble anionic polymer to form a liquid formulation.

Also provided is a pharmaceutical composition that includes sodium picosulfate, magnesium oxide, citric acid and at least one precipitation inhibitor selected from a carboxylic acid, an ammonium salt and a soluble anionic polymer. The pharmaceutical composition can, for example, be a mixture of dry ingredients that forms a liquid formulation as described herein when it is dissolved.

Also provided is a liquid pharmaceutical composition prepared by the methods described herein.

The carboxylic acid, ammonium salt and soluble anionic polymer can be any of the carboxylic acids, ammonium salts and soluble anionic polymers described herein, including combinations thereof.

In some embodiments, the precipitation inhibitor is malonic acid or tartaric acid if the liquid formulation does not comprise an ammonium salt or a soluble anionic polymer.

The ingredients can be added to the formulation and/or dissolved in any suitable combination or order. For example, the ingredients (or a sub-set of the ingredients) can be mixed as a dry formulation, before dissolving, or any of the ingredients can be added sequentially. If required, heating can be used to dissolve some of the ingredients, although heating is preferably not applied once the sodium picosulfate has been dissolved. Suitable methods of preparing the formulations are described in the Examples.

In some embodiments, the soluble anionic polymer (if included) is dissolved first, followed by a mixture comprising magnesium oxide and citric acid. Other precipitation inhibitors can be added, followed by sodium picosulfate.

If necessary the pH of the formulation can be adjusted to the range from about 4.0 to about 6.5, or, preferably, from about 4.0 to about 5.5, about 4.5 to about 5.2, from about 4.7 to about 4.9, or about 4.8. The pH can be adjusted using a suitable acid and/or base (e.g., hydrochloric acid and/or sodium hydroxide). The pH can be adjusted after all the ingredients have been dissolved or, e.g., following the addition of magnesium oxide, citric acid, and precipitation inhibitor(s), but prior to addition of sodium picosulfate.

Following preparation, the liquid formulation can be packaged in a suitable container (e.g., a bottle), which can include one or two doses of the formulation, and can be sealed with a closure. A dose can be included in a volume of the liquid formulation in the range from about 50 mL to about 250 mL, e.g., from about 100 mL to about 200 mL, for example about 100 mL, about 120 mL, about 125 mL, about 140 mL, about 150 mL, about 160 mL, about 175 mL, about 180 mL, or about 200 mL, preferably about 160 mL.

Following preparation, the formulation can be stored at a temperature in the range from about 0° C. to about 30° C., e.g., about 4° C., about 5° C., about 10° C., about 15° C., about 20° C., about 21° C., about 22° C., about 23° C., about 24° C., or about 25° C.

Upon storage, the formulation can be stable for at least about thirty days, about sixty days, about 90 days, preferably at least about six months, more preferably at least about a year, or more preferably, at least about two years.

Determining the Stability of the Formulation

As described above, a problem encountered upon prolonged storage of liquid picosulfate/magnesium salt (e.g., sodium picosulfate/magnesium citrate) formulations is the formation of a precipitate (understood to contain magnesium salts) from the formulation, which can render the formulation unusable. The present disclosure has provided formulations that can have a storage life of more than about six months, more than about one year, or even more than about two years.

A challenge with the development of such formulations is testing the formulations to confirm that they have the required stability and resistance to precipitate formation. Storage for several months or years can be needed to confirm that candidate formulations have the required level of stability, which can lead to long design-make-test cycle for developing new formulations.

During the course of developing the liquid formulations disclosed herein, it has surprisingly been found that the stability of formulations with respect to precipitation formation can be predicted within a few days by subjecting the formulations to a freeze-thaw testing cycle as exemplified in Example 3 below.

The present disclosure therefore further provides a method for determining the stability of a liquid formulation comprising sodium picosulfate and magnesium citrate. The method includes: (a) freezing the liquid formulation to provide a frozen formulation; (b) thawing the frozen liquid to provide a thawed formulation; (c) determining the absence or presence of a precipitate in the thawed formulation; and (d) determining, based on the absence of a precipitate in the thawed formulation, that the liquid formulation is stable, or determining, based on the presence of a precipitate in the thawed formulation, that the liquid formulation is unstable.

The step of freezing the liquid formulation can be carried out at a temperature sufficiently low to freeze the formulation, e.g., a temperature in the range from about −40° C. to about 0° C., e.g., a temperature of about −40° C., about −30° C., about −20° C., about −15° C., about −10° C., about −5° C., or about −0° C., preferably about −20° C. The step of freezing the liquid formulation can be carried out for a period of about 1 h to about 24 h, preferably about 4 h to about 16 h, e.g., about 4 h, about 6 h, about 8 h, about 10 h, about 12 h, about 14 h, or about 16 h, more preferably about 12 h.

The step of thawing the frozen liquid can be carried out at a temperature sufficiently high to thaw the formulation, e.g., a temperature in the from about 0° C. to about 30° C., e.g., a temperature of about 0° C., about 5° C., about 10° C., about 15° C., about 20° C., about 25° C., or about 30° C., preferably about 20° C. The step of thawing the liquid formulation can be carried out for a period of about 1 h to about 24 h, preferably about 4 h to about 16 h, e.g., about 4 h, about 6 h, about 8 h, about 10 h, about 12 h, about 14 h, or about 16 h, more preferably about 8 h.

A freeze-thaw cycle is carried out by repeating the steps of freezing the liquid and thawing the frozen liquid sequentially. A step of freezing the liquid and thawing the frozen liquid is referred to as a freeze-thaw cycle. The method can include more than one freeze-thaw cycle, e.g., one, two, three, four, five, six, seven, or more cycles. The method preferably includes at least five, and more preferably five, freeze-thaw cycles.

The step of facilitating the thawed formulation can be carried out at the end of each freeze-thaw cycle (or after a number of freeze-thaw cycles), and can be facilitated by carrying out the freeze thaw cycle in a suitable transparent container such as a tube (e.g., a test tube or a centrifuge tube). The tube can typically contain, e.g., about 5 mL to about 10 mL and is dimensioned such that the liquid fills the tube to a height of about 30 mm to about 50 mm. If a precipitate is observed, the amount of precipitate can be quantitated such as by measuring the height of the precipitate in the tube. The tube can also be graduated to assist with the quantitation.

The absence of a precipitate in the thawed formulation after carrying out one or more freeze-thaw cycles (preferably five freeze-thaw cycles) indicates that the liquid formulation is stable with respect to the formation of precipitates, whereas, conversely, the presence of a precipitate in the thawed formulation, that the liquid formulation is unstable. A formulation is determined to be more stable if precipitate is absent after a greater number of freeze-thaw cycles (e.g., five or more freeze-thaw cycles) and, conversely, less stable if precipitate is present after only a few freeze-thaw cycles. A formulation is determined to be more stable if only a small amount of precipitate is formed after a given number of freeze-thaw cycles (e.g., five freeze-thaw cycles) and, conversely, less stable if a greater amount of precipitate is present after the same number of freeze-thaw cycles.

Use and Administration of the Formulation

The liquid formulation described herein can be used to treat constipation or for the clearance of the bowel prior to X-ray examination, endoscopy or surgery.

The liquid formulation containing an effective formulation containing effective amounts of picosulfate (e.g., sodium picosulfate) and magnesium (e.g., magnesium citrate) is administered to a subject (e.g., a patient) in need of the treatment.

The picosulfate salt can be present in an amount that provides a dose of sodium picosulfate, or a dose equivalent to a dose of sodium picosulfate, wherein the amount of sodium picosulfate in the dose is from about 5 mg to about 15 mg, preferably from about 8 mg to about 12 mg, about 9 mg to about 11 mg, or about 10 mg, preferably a 10 mg dose of sodium picosulfate. The magnesium salt can be present in an amount per dose that is provided, or an amount that is equivalent to the amount that is provided, when the magnesium salt is prepared from magnesium oxide and the amount of magnesium oxide is in the range from about 1 g to about 6 g, e.g., from about 2 g to about 5 g, from about 2 g to about 4 g, from about 3 g to about 5 g, or from about 3 g to about 4 g, e.g., about 1 g, about 1.5 g, about 2 g, about 2.5 g, about 3 g, about 3.5 g, about 4 g, about 4.5 g, about 5 g, about 5.5 g, or about 6 g, preferably about 3.5 g. The magnesium salt can be present as the citrate salt wherein the amount of citric acid per dose can be an amount that is provided by an amount of anhydrous citric acid (or an equivalent amount of hydrated citric acid) in the range from about 3 g to about 20 g, e.g., from about 5 g to about 15 g, from about 10 g to about 15 g, or about 9 g, about 10 g, about 11 g, about 12 g, about 13 g, about 14 g, or about 15 g, preferably about 12 g. The dose can be included in a volume of the liquid formulation in the range from about 50 mL to about 250 mL, e.g., from about 100 mL to about 200 mL, for example about 100 mL, about 120 mL, about 125 mL, about 140 mL, about 150 mL, about 160 mL, about 175 mL, about 180 mL, or about 200 mL, preferably about 160 mL.

When used for clearance of the bowel, e.g., prior to X-ray examination, endoscopy or surgery, it can be useful for two doses of the liquid formulation to be administered. For example, the following procedures may be used:

The formulation can be given a split dose administration where a first dose of the formulation is taken the evening before the procedure (e.g., between about 5 pm and about 9 pm), which can be followed administration of clear liquid (e.g., five 150 mL glasses of clear liquid). Then, a second dose of the formulation can be taken the morning of the procedure (e.g., at least 1, 2, 3, 4 or 5 hours prior to but typically no more than 8, 9 or 10 hours prior to the procedure), which can be followed by administration of clear liquid (e.g., three 150 mL glasses of clear liquid).

The formulation can also be given a split dose administration where two doses of the formulation are taken the day before the procedure. For example, one dose of the liquid formulation can be taken in the afternoon (e.g., between about 4 pm and about 6 pm), which can be followed administration of clear liquid (e.g., five 150 mL glasses of clear liquid). Then, a second dose of the formulation can be taken in the late evening (e.g., approximately 6 h later, e.g., between about 10 pm and about 12 am), which can be followed by administration of clear liquid (e.g., three 150 mL glasses of clear liquid).

EXAMPLES

The invention is further described in the following examples, which do not limit the scope of the invention described in the claims.

Example 1

Instability of Unstabilized Sodium Picosulfate/Magnesium Citrate Formulations

A liquid formulation containing sodium picosulfate and magnesium citrate was prepared by dissolving a sachet of commercially available PREPOPIK® containing sodium picosulfate (10 mg), magnesium oxide (3.5 g), citric acid (12 g), $KHCO_3$ (0.65 g), and orange or berry flavoring in water (150 mL). The solution is stored under ambient conditions and observed periodically until precipitation from the solution is noted.

Precipitation occurs within 2 days for the unstabilized sodium picosulfate/magnesium citrate formulation.

Example 2

Stability of Malic Acid Stabilized Sodium Picosulfate/Magnesium Citrate Formulations A liquid formulation containing sodium picosulfate and magnesium citrate stabilized with malic acid was prepared using the ingredients listed in Table 1. The solution is stored under ambient conditions and observed periodically for precipitation from the solution. No precipitation is observed within 340 days.

As a reference, commercially available sodium picosulfate/magnesium oxide/citric acid (PICOSOLUTION™, Pharmbio Co., Ltd.) is also stored under ambient conditions and observed periodically for precipitation from the solution. No precipitation is observed within 645 days.

TABLE 1

Composition of a Malic Acid Stabilized Sodium Picosulfate/Magnesium Citrate Formulations

| Ingredients | Weight/Unit Dose (g) |
| --- | --- |
| Purified water | 150 |
| Disodium edetate (EDTA) | 0.07 |
| Sodium benzoate | 0.090 |
| DL-Malic Acid | 8.38 |

TABLE 1-continued

Composition of a Malic Acid Stabilized Sodium
Picosulfate/Magnesium Citrate Formulations

| Ingredients | Weight/Unit Dose (g) |
|---|---|
| Citric acid, anhydrous | 12.00 |
| Magnesium oxide | 3.50 |
| Sucralose | 0.200 |
| Acesulfame potassium | 0.200 |
| Berry flavor | 0.120 |
| Sodium hydroxide (pellets) | 4.560 |
| Sodium picosulfate | 0.010 |

Example 3

Accelerated Method for Predicting Precipitation of Picosulfate/Magnesium Citrate Formulations An accelerated method for predicting precipitation of picosulfate/magnesium citrate formulations by using freeze-thaw cycles was developed.

A picosulfate formulation containing sodium picosulfate (10 mg), magnesium oxide (3.5 g), citric acid (12 g), and KHCO$_3$ (0.65 g) and, optionally, a precipitation inhibitor (or combination of inhibitors) to be tested, dissolved in water (150 mL) is prepared. The pH is adjusted to the range 4.7-5.1 using aq. NaOH and aq. HCl solutions. The solution is filtered through a 0.22 μm PTFE filter under vacuum.

Two portions of 10 mL of the formulation test solution are placed in tapered, graduated, centrifuge tubes (15 mL) and subjected to five freeze-thaw cycles in which the solutions are frozen at −20° C. for at least 12 h and then thawed at 20-25° C. for 8 h. At the end of each cycle, the tube is inspected for precipitation at the bottom of the tube. If precipitation is present, the amount of precipitate is quantitated by measuring the height (in mm) of the precipitate in the centrifuge tube using a ruler.

The remainder of the formulation test solution may be stored at ambient temperature (e.g., 20-25° C.) to determine the stability under non-accelerated conditions.

Example 4

Correlation Between Freeze-Thaw Cycle Accelerated Method and Precipitation Upon Storage Under Ambient Conditions Solutions of PREPOPIK® orange or berry flavor containing sodium picosulfate (10 mg), magnesium oxide (3.5 g), citric acid (12 g), and KHCO$_3$ (0.65 g) in water (150 mL) as described in Example 1, commercially available PICOSOLUTION™ sodium picosulfate liquid formulation, and malic-acid stabilized sodium picosulfate/magnesium citrate formulation (Example 2, Table 1) are placed in 15 mL tapered, graduated centrifuge tubes (2×10 mL portions for each solution) and subjected to freeze thaw cycling as described in Example 3. The amount of precipitate (if any) is quantitated by measuring the height (in mm) of the precipitate in the centrifuge tube using a ruler at the end of each freeze thaw cycle. The results for each of the solutions are summarized in Table 2.

Samples of each of the solutions are also stored at ambient temperature (20-25° C.) and monitored for the appearance of precipitation.

For the PREPOPIK® orange or berry flavor formulations, the presence of precipitate is observed after 2 days.

No precipitate is observed for the commercially available PICOSOLUTION™ sodium picosulfate liquid formulation (no precipitate seen after storage for 645 days).

Precipitation is also not observed for the malic-acid stabilized sodium picosulfate/magnesium citrate formulation (Example 2, Table 1) (no precipitate seen after storage for 340 days). The results of the room temperature storage experiment is also summarized in Table 2.

TABLE 2

Correlation between Freeze-Thaw Cycle Accelerated Method
and Precipitation upon Storage under Ambient Conditions

| Formulations | Precipitation after Freeze-Thaw Cycles (mm) | | | | | Time to ppt. (Ambient Temp.) |
|---|---|---|---|---|---|---|
| | 1st Cycle | 2nd Cycle | 3rd Cycle | 4th Cycle | 5th Cycle | |
| PREPOPIK® Berry Flavor | 5.4 | 26.3 | 38.4 | 38.9 | 38.0 | 2 d |
| PREPOPIK® Orange Flavor | 2.0 | 4.5 | 36.5 | 37.5 | 37.5 | 2 d |
| PICOSOLUTION™ sodium picosulfate/magnesium citrate | 0 | 0 | 0 | 0 | 0 | >645 d |
| Malic acid stabilized sodium picosulfate/magnesium citrate | 0 | 0 | 0 | 0 | 0 | >340 d |

The data show that the accelerated freeze-thaw method can be used to predict whether a sodium picosulfate/magnesium citrate liquid formulation will be stable with respect to the formation of precipitate upon prolonged storage under ambient conditions.

Examples 5-8

Stabilized Sodium Picosulfate/Magnesium Citrate Formulations Containing Malic Acid as a Precipitation Inhibitor A liquid formulation containing sodium picosulfate and magnesium citrate is prepared by dissolving a sachet of commercially available PREPOPIK® containing sodium picosulfate (10 mg), magnesium oxide (3.5 g), citric acid (12 g), KHCO$_3$ (0.65 g), and berry flavoring, in water (150 mL). Malic acid (31 to 78 mmol per sachet of PREPOPIK®) is added, and the pH is adjusted to the range 4.7-5.1 using aq. NaOH and aq. HCl solutions. The solution is filtered through a 0.22 μm PTFE filter under vacuum.

The resulting solution is subjected to testing under the freeze-thaw conditions as described in Example 3 or stored under ambient conditions.

The amount of precipitate measured after five freeze-thaw cycles or the number of days until precipitation was observed for solutions containing various amounts of malic acid is shown in Table 3.

TABLE 3

Stabilized Sodium Picosulfate/Magnesium Citrate Formulations
Containing Malic Acid as a Precipitation Inhibitor.

| Ex. | Malic Acid (mmol per 150 mL) | Precipitation after 5 freeze-thaw cycles (mm) | Time to ppt. (Ambient temp.) |
|---|---|---|---|
| Reference | 0 | 38.0 | 2 d |
| 5 | 31 | 18.0 | 34 d |

TABLE 3-continued

Stabilized Sodium Picosulfate/Magnesium Citrate Formulations Containing Malic Acid as a Precipitation Inhibitor.

| Ex. | Malic Acid (mmol per 150 mL) | Precipitation after 5 freeze-thaw cycles (mm) | Time to ppt. (Ambient temp.) |
|---|---|---|---|
| 6 | 47 | 2.5 | 39 d |
| 7 | 63 | 0.0 | >158 d |
| 8 | 78 | 0.0 | >144 d |

The results show that malic acid is effective to inhibit precipitation of sodium picosulfate/magnesium sulfate concentrations, although quite high concentrations of malic acid (63 mmol per 150 mL, 0.42 M or greater) are needed for prolonged stability.

Examples 9-13

Stabilized Sodium Picosulfate/Magnesium Citrate Formulations Containing Carboxylic Acids as Precipitation Inhibitors The carboxylic acid is dissolved in water (150 mL) until a clear solution is formed. A sachet of PREPOPIK® sodium picosulfate/magnesium citrate granules (containing sodium picosulfate (10 mg), magnesium oxide (3.5 g, citric acid (12 g), KHCO$_3$ (0.65 g), Na-saccharin and orange flavoring is added. NaOH is added to adjust the pH of the solution. The solutions are stored at 6° C. and observed periodically until precipitation from the solution is noted. The results for various carboxylic acids are shown in Table 4.

TABLE 4

Carboxylic Acid-Stabilized Sodium Picosulfate/Magnesium Citrate Formulations Containing Sodium Picosulfate (10 mg), Magnesium Oxide (3.5 g, Citric Acid (12 g), KHCO$_3$ (0.65 g) and Carboxylic Acids in 150 mL Water

| Ex. | Acid | NaOH (g) | pH | Time to Ppt (d) |
|---|---|---|---|---|
| 9 | Ascorbic acid (12.89 g; 73 mmol) | 2.32 | 4.8 | 10 |
| 10 | Ascorbic acid (8.59 g; 49 mmol) | 1.51 | 4.8 | 8 |
| 11 | Succinic acid (4.32 g; 37 mmol) | 2.28 | 5.1 | 10 |
| 12 | Tartaric acid (5.49 g; 37 mmol) | 3.20 | 6.0 | 60 |
| 13 | Aspartic acid (4.87 g; 37 mmol) | 1.27 | 4.8 | 20 |

Examples 14-46

Stabilized Sodium Picosulfate/Magnesium Citrate Formulations Containing Carboxylic Acids as Precipitation Inhibitors A liquid formulation containing sodium picosulfate and magnesium citrate is prepared by dissolving a sachet of commercially available PREPOPIK® containing sodium picosulfate (10 mg), magnesium oxide (3.5 g), citric acid (12 g), KHCO$_3$ (0.65 g), and orange or berry flavoring, in water (150 mL). A carboxylic acid (63 mmol per sachet of PREPOPIK®) is added, and the pH is adjusted to the range 4.7-5.1 using aq. NaOH and aq. HCl solutions. The solution is filtered through a 0.22 µm PTFE filter under vacuum.

The resulting solution is subjected to testing under the freeze-thaw conditions as described in Example 3 or stored under ambient conditions.

The amount of precipitate measured after five freeze-thaw cycles observed for solutions containing various carboxylic acids is shown in Table 5. Each of the acids for which precipitation is observed after the 5th freeze-thaw cycle also exhibits precipitation within 60 days upon storage at room temperature.

TABLE 5

Precipitation of Stabilized Sodium Picosulfate/Magnesium Citrate Formulations Containing Carboxylic Acids as Precipitation Inhibitors.

| | | | Precipitation after Freeze-Thaw Cycles (mm) | | | | |
|---|---|---|---|---|---|---|---|
| Ex. | Precipitation Inhibitor[a] | PREPOPIK® Flavor | 1st Cycle | 2nd Cycle | 3rd Cycle | 4th Cycle | 5th Cycle |
| Ref. | None | Orange | 2.0 | 4.5 | 36.5 | 37.5 | 37.5 |
| Ref. | None | Berry | 3.0 | 10.5 | 39.0 | 39.0 | 39.0 |
| Ref. | None | Berry | 5.0 | 35.5 | 38.5 | 38.5 | 36.0 |
| Ref. | None | Berry | 5.5 | 22.5 | 38.0 | 40.0 | 41.5 |
| Ref. | None | Berry | 8.0 | 36.5 | 38.0 | 38.0 | 35.5 |
| 14 | L-Tryptophan | Berry | 14.5 | 25.5 | 35.0 | 36.0 | 38.0 |
| 15 | L-Glutamine | Berry | 22.0 | 29.0 | 30.0 | 33.5 | 36.5 |
| 16 | L-Threonine | Berry | 1.0 | 8.5 | 20.0 | 28.5 | 33.0 |
| 17 | Propionic acid | Berry | 0.5 | 12.5 | 13.5 | 31.5 | 32.0 |
| 18 | L-Tyrosine | Berry | 14.0 | 22.0 | 35.0 | 32.0 | 31.0 |
| 19 | L-Glutamic acid | Berry | 10.0 | 17.0 | 22.0 | 28.0 | 30.5 |
| 20 | DL-Cysteine | Berry | 4.0 | 7.0 | 15.0 | 17.5 | 30.0 |
| 21 | Glutaric acid | Berry | 6.0 | 18.5 | 26.0 | 27.5 | 29.5 |
| 22 | DL-Asparagine monohydrate | Berry | 5.0 | 11.0 | 20.0 | 24.0 | 29.0 |
| 23 | Succinic acid | Berry | 5.0 | 15.0 | 23.0 | 25.0 | 28.5 |
| 24 | Acetic acid | Berry | 14.0 | 25.5 | 29.0 | 28.0 | 28.0 |
| 25 | Ascorbic acid | Berry | 10.3 | 23.0 | 26.0 | 28.0 | 28.0 |
| 26 | Maleic acid | Orange | 4.0 | 18.0 | 27.0 | 28.0 | 28.0 |
| 27 | Lactic acid | Berry | 4.0 | 15.0 | 19.5 | 24.0 | 25.5 |
| 28 | L-Methionine | Berry | 25.5 | 29.0 | 26.5 | 25.0 | 24.5 |
| 29 | Glucuronic acid | Orange | 6.0 | 12.5 | 15.5 | 17.0 | 21.5 |
| 30 | L-Lysine monohydrate | Berry | 2.0 | 15.0 | 17.5 | 18.0 | 21.5 |
| 31 | Fumaric acid | Orange | 2.0 | 8.0 | 14.0 | 16.0 | 20.5 |
| 32 | Histidine | Orange | 1.0 | 6.0 | 8.5 | 14.5 | 13.0 |

TABLE 5-continued

Precipitation of Stabilized Sodium Picosulfate/Magnesium Citrate Formulations Containing Carboxylic Acids as Precipitation Inhibitors.

| Ex. | Precipitation Inhibitor[a] | PREPOPIK® Flavor | 1st Cycle | 2nd Cycle | 3rd Cycle | 4th Cycle | 5th Cycle |
|---|---|---|---|---|---|---|---|
| 33 | L-Arginine | Berry | 3.3 | 8.0 | 10.0 | 10.5 | 10.5 |
| 34 | L-Aspartic acid | Berry | 0.0 | 1.5 | 4.5 | 7.5 | 10.5 |
| 35 | Formic acid | Orange | 0.0 | 3.0 | 5.5 | 7.0 | 8.5 |
| 36 | Serine | Orange | 0.0 | 2.0 | 3.0 | 5.0 | 8.5 |
| 37 | Sodium gluconate | Berry | 0.0 | 0.0 | 2.0 | 3.0 | 6.5 |
| 38 | Gluconic acid | Orange | 0.0 | 2.0 | 3.0 | 3.0 | 5.5 |
| 39 | Glycolic acid | Orange | 0.0 | 0.0 | 1.5 | 3.8 | 5.5 |
| 40 | Citric acid | Berry | 2.0 | 2.0 | 3.5 | 3.5 | 4.5 |
| 41 | Malic acid | Berry | 0.0 | 0.0 | 0.0 | 0.0 | 0.0 |
| 42 | Malic acid | Berry | 0.0 | 0.0 | 0.0 | 0.0 | 0.0 |
| 43 | Malic acid | Berry | 0.0 | 0.0 | 0.0 | 0.0 | 0.0 |
| 44 | Malic acid | Berry | 0.0 | 0.0 | 0.0 | 0.0 | 0.0 |
| 45 | Malonic acid | Berry | 0.0 | 0.0 | 0.0 | 0.0 | 0.0 |
| 46 | Tartaric acid | Berry | 0.0 | 0.0 | 0.0 | 0.0 | 0.0 |

[a]63 mmol in 150 mL of the composition.

The results show that, in addition to malic acid, malonic acid and tartaric acid also were very effective to inhibit precipitation of sodium picosulfate/magnesium citrate compositions.

Examples 47-54

Stabilized Sodium Picosulfate/Magnesium Citrate Formulations Containing Malic Acid, Malonic Acid, Tartaric Acid or Succinic Acid-As Precipitation Inhibitors A liquid formulation containing sodium picosulfate and magnesium citrate is prepared by dissolving a sachet of commercially available PREPOPIK® containing sodium picosulfate (10 mg), magnesium oxide (3.5 g), citric acid (12 g), $KHCO_3$ (0.65 g), and orange flavoring, in water (150 mL). Malic acid, malonic acid, tartaric acid, or succinic acid (31-63 mmol per sachet of PREPOPIK®) is added, and the pH is adjusted to the range 4.7-5.1 using aq. NaOH and aq. HCl solutions. The solution is filtered through a 0.22 μm PTFE filter under vacuum.

The resulting solution is subjected to testing under the freeze-thaw conditions as described in Example 3.

The amount of precipitate measured after five freeze-thaw cycles for solutions containing various amounts of malic acid is shown in Table 6.

TABLE 6

Precipitation of Stabilized Sodium Picosulfate/Magnesium Citrate Formulations Containing Carboxylic Acids as Precipitation Inhibitors.

| Ex. | Precipitation Inhibitor | Amount (mmol) in 150 mL | 1st Cycle | 2nd Cycle | 3rd Cycle | 4th Cycle | 5th Cycle |
|---|---|---|---|---|---|---|---|
| 47 | Malic acid | 63 | 0.0 | 0.0 | 0.0 | 0.0 | 0.0 |
| 48 | Malic acid | 31 | 1.5 | 6.0 | 16.5 | 18.0 | 20.0 |
| 49 | Malonic acid | 63 | 0.0 | 0.0 | 0.0 | 0.0 | 0.0 |
| 50 | Malonic acid | 31 | 0.0 | 0.5 | 1.0 | 4.0 | 4.0 |
| 51 | Tartaric acid | 63 | 0.0 | 0.0 | 0.0 | 0.0 | 0.0 |
| 52 | Tartaric acid | 31 | 0.0 | 9.5 | 15.5 | 18.5 | 20.0 |
| 53 | Succinic acid | 63 | 0.5 | 8.5 | 15.5 | 19 | 22.5 |
| 54 | Succinic acid | 125 | 0 | 0 | 1.5 | 3 | 4 |

The results show that a concentration of 63 mmol in 150 mL (420 mM) of malic acid, malonic acid, or tartaric acid is effective to inhibit precipitation through the 5 day freeze-thaw cycle. The results at the lower concentration of 31 mmol in 150 mL (210 mM) indicate that malonic acid is more effective as a precipitation inhibitor than malic acid, while tartaric acid was of comparable effectiveness. The results obtained with succinic acid suggest that even the less effective precipitation inhibitors may be effective when the concentration is increased.

Examples 55-61

Stabilized Sodium Picosulfate/Magnesium Citrate Formulations Containing Anionic Polymers as Precipitation Inhibitors Polymer (0.15 g) is dissolved in water (150 mL) until a clear solution is formed. A sachet of PREPOPIK® sodium picosulfate/magnesium citrate granules (containing sodium picosulfate (10 mg), magnesium oxide (3.5 g), citric acid (12 g), $KHCO_3$ (0.65 g), Na-saccharin and orange flavoring) is added. In a control experiment, a reference formulation is prepared by dissolving a sachet of PREPOPIK® in the absence of polymer. The solutions are stored at 6° C. and observed periodically until precipitation from the solution is noted. The results for various polymers are shown in Table 7.

TABLE 7

Polymer-Stabilized Sodium Picosulfate/Magnesium Citrate Formulations For Solutions Containing Sodium Picosulfate (10 mg), Magnesium Oxide (3.5 g, Citric Acid (12 g), KHCO$_3$ (0.65 g) and Polymer (0.15 g) in 150 mL Water (pH 4.8)

| Ex. | Polymer | Time to Ppt (d) |
|---|---|---|
| Ref.* | None | 2 |
| 55 | Hydroxypropylcellulose (KLUCEL HXF) | 2 |
| 56 | Povidone, USP (KOLLIDONE 30) | 2 |
| 57 | HPMC (VIVAPHARM, HPMC E5) | 7 |
| 58 | HPMC (METHOCEL K4M PREM CR) | 7 |
| 59 | Sodium alginate (PROTANAL ® CR 8133) | 25 |
| 60 | Sodium alginate (PROTANAL ® CR8233) | 20 |
| 61 | Xanthan gum (XANTURAL ® 75) | 20 |

*PREPOPIK ® without added polymer.

Examples 62-73

Stabilized Sodium Picosulfate/Magnesium Sulfate Formulations Containing Anionic Polymers as Precipitation Inhibitors A polymer (15-300 mg) is dissolved in water (150 mL) until a clear solution (containing the polymer at a concentration of 0.1-2% (w/v) is formed. A sachet of PREPOPIK® sodium picosulfate/magnesium citrate granules (containing sodium picosulfate (10 mg), magnesium oxide (3.5 g), citric acid (12 g), KHCO$_3$ (0.65 g), Na-saccharin and orange flavoring) is added, and the pH is adjusted to the range 4.7-5.1 using aq. NaOH and aq. HCl solutions. The solution is filtered through a 0.22 μm PTFE filter under vacuum.

The resulting solution is subjected to testing under the freeze-thaw conditions as described in Example 3.

The amount of precipitate measured after five freeze-thaw cycles for solutions containing various polymers is shown in Table 8.

TABLE 8

Precipitation of Stabilized Sodium Picosulfate/Magnesium Citrate Formulations Containing Anionic Polymers as Precipitation Inhibitors.

| Ex. | Precipitation Inhibitor | Conc. Of Polymer (% w/v) | 1st Cycle | 2nd Cycle | 3rd Cycle | 4th Cycle | 5th Cycle |
|---|---|---|---|---|---|---|---|
| Ref. | None | — | 2.0 | 4.5 | 36.5 | 37.5 | 37.5 |
| 62 | Sodium carboxymethyl-cellulose (AQUALON ® CMC-7L2P) | 0.5% | 7.8 | 26.3 | 29.0 | 29.8 | 30.0 |
| 63 |  | 1.0% | 8.8 | 19.8 | 24.8 | 27.0 | 30.3 |
| 64 |  | 2.0% | 7.5 | 19.5 | 23.5 | 25.0 | 25.5 |
| 65 | Sodium alginate (PROTANAL ® CR 8133) | 0.5% | 1.8 | 6.5 | 18.3 | 25.3 | 27.0 |
| 66 |  | 1.0% | 0.0 | 0.3 | 1.0 | 3.0 | 3.5 |
| 67 | Carrageenan (VISCARIN ® GP 109 NF) | 0.5% | 0.0 | 2.0 | 21.0 | 23.3 | 26.0 |
| 68 |  | 1.0% | 0.0 | 0.0 | 0.0 | 1.0 | 3.0 |
| 69 | Xanthan gum (XANTURAL ® 75) | 0.1% | 4.4 | 10.0 | 17.8 | 22.3 | 27.5 |
| 70 |  | 0.5% | 0.0 | 0.0 | 0.0 | 0.0 | 0.0 |
| 71 |  | 1.0% | 0.0 | 1.0 | 5.0 | 5.0 | 5.0 |
| 72 | CARBOPOL ® 71G NF | 0.1% | 0.0 | 30.5 | 35.5 | 41.0 | 39.0 |
| 73 |  | 0.2% | 19.0 | 31.0 | 38.0 | 43.5 | 47.5 |

The anionic polymers are effective to inhibit precipitation, with sodium alginate, carrageenan and xanthan gum being particularly effective. While not being limited by any theory, the limited effectiveness of CARBOPOL® 71G NF (carbomer homopolymer type A, a high molecular weight polymer of acrylic acid cross-linked with allyl ethers of pentaerythritol) is understood to be due to the low solubility and low concentrations obtainable with this polymer.

Examples 74-91

Effect of Carboxylic Acid and Polymers in Inhibiting Precipitation of Magnesium Salts From Solutions Containing Magnesium Citrate Carboxylic acid or polymer is dissolved in water (80 mL), with heating of the solution for Ex. 80-83, 86 and 87. Citric acid (6.4 g) is added, followed by magnesium oxide (1.87 g) and, KHCO$_3$ (0.267 g) (for Ex. 86-91 only) and NaOH to adjust the pH. The solutions are stored at 6° C. and observed periodically until precipitation from the solution is noted. The results for various formulations are shown in Table 9.

TABLE 9

Carboxylic Acid and Polymer-Stabilized Magnesium Citrate Formulations

| Ex. | Acid or Polymer | KHCO$_3$ (g) | NaOH (g) | Heat | pH | Time to Ppt (d) |
|---|---|---|---|---|---|---|
| 74 | Acetic acid (1.56 g; 26 mmol) |  |  | no | 3.9 | 25 |
| 75 | Ascorbic acid (4.58 g; 26 mmol) |  |  | no | 3.9 | 25 |
| 76 | HPMC (VIVAPHARM, HPMC E5) (0.08 g) |  |  | no | 4.3 | 5 |
| 77 | Sodium Alginate (PROTANAL ® CR 8133) (0.08 g) |  |  | no | 4.4 | 25 |
| 78 | Acetic acid (2.34 g; 39 mmol) |  |  | no | 3.8 | 25 |
| 79 | Ascorbic acid (6.87 g; 39 mmol) |  |  | no | 3.8 | 130 |
| 80 | Acetic acid (1.56 g; 26 mmol) |  |  | yes | 4.0 | 20 |
| 81 | Acetic acid (2.34 g; 39 mmol) |  |  | yes | 3.9 | 130 |
| 82 | Ascorbic acid (4.58 g; 26 mmol) |  |  | yes | 3.9 | 20 |
| 83 | Ascorbic acid (6.87 g; 39 mmol) |  |  | yes | 3.8 | 130 |
| 84 | HPMC (VIVAPHARM, HPMC E5) (0.08 g) |  |  | no | 4.3 | 5 |
| 85 | Sodium alginate (PROTANAL ® CR 8133) (0.08 g) |  |  | no | 4.3 | 20 |
| 86 | Sodium alginate (PROTANAL ® CR 8133) (0.08 g) | 0.267 | 0.25 | yes | 4.8 | 2 |
| 87 | Sodium alginate (PROTANAL ® CR 8133) (0.08 g) | 0.267 | 1.25 | yes | 4.9 | 15 |
| 88 | Lactic acid (2.34 g; 90 mmol) | 0.267 | 1.18 | no | 5.1 | 15 |
| 89 | Succinic acid (1.54 g; 13 mmol) | 0.267 | 0.81 | no | 4.8 | 10 |
| 90 | Tartaric acid (1.95 g; 13 mmol) | 0.267 | 1.03 | no | 4.7 | 30 |
| 91 | Aspartic acid (1.73 g; 13 mmol) | 0.267 | 0.57 | no | 4.7 | 13 |

Examples 92-105

Sodium Alginate Stabilized Sodium Picosulfate/Magnesium Citrate Formulations Solutions are prepared as follows:
1. Sodium alginate is dissolved in water at ambient temperature.
2. Citric acid is added.
3. Magnesium oxide is added, and the solution is heated until clear, then allowed to cool to ambient temperature.
4. KHCO$_3$ is added.
5. Sodium chloride (optional) is added.
6. Na-saccharin, EDTA (optional), methyl paraben, propyl paraben, and flavor are added.
7. NaOH is added to adjust the pH.
6. Sodium picosulfate is added.

The solutions are stored at 6° C. and observed periodically until precipitation from the solution is noted. The results for various formulations are shown in Tables 10A and 10B.

TABLE 10A

Sodium Alginate-Stabilized Sodium Picosulfate/Magnesium Citrate Formulations

| Example | 92 | 93 | 94 | 95 | 96 | 97 |
|---|---|---|---|---|---|---|
| Water (mL) | 80 | 80 | 80 | 80 | 80 | 80 |
| Sodium alginate (PROTANAL ® CR 8133) (g) | 0.0813 | 0.163 | 0.244 | 0.0813 | 0.163 | 0.244 |
| Citric acid (g) | 6.4 | 6.4 | 6.4 | 6.4 | 6.4 | 6.4 |
| Magnesium oxide (g) | 1.87 | 1.87 | 1.87 | 1.87 | 1.87 | 1.87 |
| KHCO$_3$ | 0.267 | 0.267 | 0.267 | 0.267 | 0.267 | 0.267 |
| Na-saccharin | 0.032 | 0.032 | 0.032 | 0.032 | 0.032 | 0.032 |
| Methyl paraben | 0.08 | 0.08 | 0.08 | 0.08 | 0.08 | 0.08 |
| Propyl paraben | 0.016 | 0.016 | 0.016 | 0.016 | 0.016 | 0.016 |
| Berry flavor | 0.065 | 0.065 | 0.065 | | | |
| Orange flavor | | | | 0.033 | 0.033 | 0.033 |
| EDTA | | | | 0.028 | 0.028 | 0.028 |
| NaOH | 0.03 | 0.09 | 0.09 | 0.09 | 0.08 | 0.09 |
| Sodium picosulfate | 0.0055 | 0.0055 | 0.0055 | 0.0055 | 0.0055 | 0.0055 |
| pH | 4.5 | 4.5 | 4.5 | 4.5 | 4.5 | 4.5 |
| Time to ppt (d) | 8 | 5 | 20 | 7 | 7 | 7 |

Examples 106-113

Sodium Alginate and Sodium Acetate Stabilized Sodium Picosulfate/Magnesium Citrate Formulations Solutions are prepared as follows:
1. Sodium alginate and EDTA dissolved in water at ambient temperature.
2. Citric acid, magnesium oxide, methyl paraben and propyl paraben are added and the solution is heated until clear, then allowed to cool to ambient temperature.
3. Sodium acetate trihydrate is added.
4. KHCO$_3$ is added.
5. Na-saccharin is added.
6. The pH is adjusted with HCl (12 M) and/or NaOH.
7. Flavor is added.
8. Sodium picosulfate is added.

The solutions are stored at 6° C. and observed periodically until precipitation from the solution is noted. The results for various formulations are shown in Table 11.

TABLE 10B

Sodium Alginate-Stabilized Sodium Picosulfate/Magnesium Citrate Formulations (Containing Sodium Chloride)

| Example | 98 | 99 | 100 | 101 | 102 | 103 | 104 | 105 |
|---|---|---|---|---|---|---|---|---|
| Water (mL) | 80 | 80 | 80 | 80 | 80 | 80 | 80 | 80 |
| Sodium alginate (PROTANAL ® CR 8133) (g) | 0.813 | 0.163 | 0.813 | 0.163 | 0.813 | 0.163 | 0.813 | 0.163 |
| Citric acid (g) | 6.4 | 6.4 | 6.4 | 6.4 | 6.4 | 6.4 | 6.4 | 6.4 |
| Magnesium oxide (g) | 1.87 | 1.87 | 1.87 | 1.87 | 1.87 | 1.87 | 1.87 | 1.87 |
| KHCO$_3$ (g) | 0.267 | 0.267 | 0.267 | 0.267 | 0.267 | 0.267 | 0.267 | 0.267 |
| Sodium chloride | 1.54 | 1.54 | 2.32 | 2.32 | 1.54 | 1.54 | 2.32 | 2.32 |
| Na-saccharin (g) | 0.065 | 0.065 | 0.065 | 0.065 | 0.065 | 0.065 | 0.065 | 0.0650 |
| Methyl paraben (g) | 0.08 | 0.08 | 0.08 | 0.08 | 0.08 | 0.08 | 0.08 | 0.08 |
| Propyl paraben (g) | 0.016 | 0.016 | 0.016 | 0.016 | 0.016 | 0.016 | 0.016 | 0.016 |
| Berry flavor (g) | 0.065 | 0.065 | 0.065 | 0.065 | | | | |
| Orange flavor (g) | | | | | 0.033 | 0.033 | 0.033 | 0.033 |
| EDTA (g) | 0.028 | 0.028 | 0.028 | 0.028 | 0.028 | 0.028 | 0.028 | 0.028 |
| NaOH (g) | 0.13 | 0.13 | 0.12 | 0.13 | 0.13 | 0.13 | 0.12 | 0.13 |
| Sodium picosulfate | 0.0055 | 0.0055 | 0.0055 | 0.0055 | 0.0055 | 0.0055 | 0.0055 | 0.0055 |
| pH | 4.6 | 4.6 | 4.5 | 4.6 | 4.6 | 4.6 | 4.5 | 4.6 |
| Time to ppt (d) | 6 | 6 | 6 | 6 | 20 | 20 | 25 | 20 |

TABLE 11

Sodium Alginate and Sodium Acetate-Stabilized Sodium Picosulfate/Magnesium Citrate Formulations

| Example | 106 | 107 | 108 | 109 | 110 | 111 | 112 | 113 |
|---|---|---|---|---|---|---|---|---|
| Water (mL) | 80 | 80 | 80 | 80 | 80 | 80 | 80 | 80 |
| Sodium alginate (PROTANAL ® CR 8133) (g) | 0.813 | 0.163 | 0.813 | 0.163 | 0.813 | 0.163 | 0.813 | 0.163 |
| Sodium acetate trihydrate (g) | 5.39 | 5.39 | 8.98 | 8.98 | 5.39 | 5.39 | 8.98 | 8.98 |
| Citric acid (g) | 6.4 | 6.4 | 6.4 | 6.4 | 6.4 | 6.4 | 6.4 | 6.4 |
| Magnesium oxide (g) | 1.87 | 1.87 | 1.87 | 1.87 | 1.87 | 1.87 | 1.87 | 1.87 |
| $KHCO_3$ (g) | 0.267 | 0.267 | 0.267 | 0.267 | 0.267 | 0.267 | 0.267 | 0.267 |
| Na-saccharin (g) | 0.065 | 0.065 | 0.065 | 0.065 | 0.065 | 0.065 | 0.065 | 0.0650 |
| Methyl paraben (g) | 0.08 | 0.08 | 0.08 | 0.08 | 0.08 | 0.08 | 0.08 | 0.08 |
| Propyl paraben (g) | 0.016 | 0.016 | 0.016 | 0.016 | 0.016 | 0.016 | 0.016 | 0.016 |
| Berry flavor (g) | 0.065 | 0.065 | 0.065 | 0.065 | | | | |
| Orange flavor (g) | | | | | 0.033 | 0.033 | 0.033 | 0.033 |
| EDTA (g) | 0.028 | 0.028 | 0.028 | 0.028 | 0.028 | 0.028 | 0.028 | 0.028 |
| HCl (12M) (mL) | 1.00 | 1.00 | 1.25 | 1.25 | 1.00 | 1.00 | 1.25 | 1.25 |
| NaOH (g) | 0.00 | 0.06 | 0.00 | 0.00 | 0.00 | 0.06 | 0.00 | 0.00 |
| Sodium picosulfate (g) | 0.0055 | 0.0055 | 0.0055 | 0.0055 | 0.0055 | 0.0055 | 0.0055 | 0.0055 |
| pH | 4.8 | 4.7 | 4.9 | 4.9 | 4.8 | 4.7 | 4.9 | 4.9 |
| Time to ppt (d) | 25 | 20 | 40 | 40 | 20 | 20 | 25 | 20 |

Examples 114-121

Sodium Alginate and Sodium Lactate Stabilized Sodium Picosulfate/Magnesium Citrate Formulations Solutions are prepared as follows:
1. Sodium alginate and EDTA are dissolved in water at ambient temperature.
2. Citric acid, magnesium oxide, methyl paraben, propyl paraben and lactic acid are added and the solution is heated until clear, then allowed to cool to ambient temperature.
3. Sodium lactate is added.
4. $KHCO_3$ is added.
5. Na-saccharin is added.
6. The pH is adjusted with NaOH.
7. Flavor is added.
8. Sodium picosulfate is added.

The solutions are stored at 6° C. and observed periodically until precipitation from the solution is observed. The results for various formulations are shown in Table 12.

Examples 122-129

Sodium Alginate and Sodium Gluconate Stabilized Sodium Picosulfate/Magnesium Citrate Formulations Solutions are prepared as follows:
1. Sodium alginate and EDTA are dissolved in water at ambient temperature.
2. Sodium gluconate is added and dissolved.
3. The pH is adjusted to below 2.5 with HCl (12 M).
4. Citric acid, magnesium oxide, methyl paraben, propyl paraben and lactic acid are added and the solution is heated until clear, then allowed to cool to ambient temperature.
5. $KHCO_3$ is added.
6. Na-saccharin is added.
7. The pH is adjusted with NaOH.
8. Flavor is added.
9. Sodium picosulfate is added.

The solutions are stored at 6° C. and observed periodically until precipitation from the solution is noted. The results for various formulations are shown in Table 13.

TABLE 12

Sodium Alginate and Sodium Lactate-Stabilized Sodium Picosulfate/Magnesium Citrate Formulations

| Example | 114 | 115 | 116 | 117 | 118 | 119 | 120 | 121 |
|---|---|---|---|---|---|---|---|---|
| Water (mL) | 80 | 80 | 80 | 80 | 80 | 80 | 80 | 80 |
| Sodium alginate (PROTANAL ® CR 8133) (g) | 0.813 | 0.163 | 0.813 | 0.163 | 0.813 | 0.163 | 0.813 | 0.163 |
| Lactic acid (g) | 3.25 | 3.25 | 2.44 | 2.44 | 3.25 | 3.25 | 2.44 | 2.44 |
| Sodium lactate (g) | 2.71 | 2.71 | 2.03 | 2.03 | 2.71 | 2.71 | 2.03 | 2.03 |
| Citric acid (g) | 6.4 | 6.4 | 6.4 | 6.4 | 6.4 | 6.4 | 6.4 | 6.4 |
| Magnesium oxide (g) | 1.87 | 1.87 | 1.87 | 1.87 | 1.87 | 1.87 | 1.87 | 1.87 |
| $KHCO_3$ (g) | 0.267 | 0.267 | 0.267 | 0.267 | 0.267 | 0.267 | 0.267 | 0.267 |
| Na-saccharin (g) | 0.065 | 0.065 | 0.065 | 0.065 | 0.065 | 0.065 | 0.065 | 0.065 |
| Methyl paraben (g) | 0.08 | 0.08 | 0.08 | 0.08 | 0.08 | 0.08 | 0.08 | 0.08 |
| Propyl paraben (g) | 0.016 | 0.016 | 0.016 | 0.016 | 0.016 | 0.016 | 0.016 | 0.016 |
| Berry flavor (g) | 0.065 | 0.065 | 0.065 | 0.065 | | | | |
| Orange flavor (g) | | | | | 0.033 | 0.033 | 0.033 | 0.033 |
| EDTA (g) | 0.028 | 0.028 | 0.028 | 0.028 | 0.028 | 0.028 | 0.028 | 0.028 |
| NaOH (g) | 0.27 | 0.27 | 0.29 | 0.28 | 0.27 | 0.27 | 0.29 | 0.31 |
| Sodium picosulfate (g) | 0.0055 | 0.0055 | 0.0055 | 0.0055 | 0.0055 | 0.0055 | 0.0055 | 0.0055 |
| pH | 4.7 | 4.7 | 4.7 | 4.8 | 4.7 | 4.7 | 4.7 | 4.8 |
| Time to ppt (d) | 15 | 20 | 15 | 20 | 15 | 15 | 15 | 15 |

TABLE 13

Sodium Alginate and Sodium Gluconate-Stabilized Sodium Picosulfate/Magnesium Citrate Formulations

| Example | 122 | 123 | 124 | 125 | 126 | 127 | 128 | 129 |
|---|---|---|---|---|---|---|---|---|
| Water (mL) | 80 | 80 | 80 | 80 | 80 | 80 | 80 | 80 |
| Sodium alginate (PROTANAL ® CR 8133) (g) | 0.813 | 0.163 | 0.813 | 0.163 | 0.813 | 0.163 | 0.813 | 0.163 |
| Sodium gluconate (g) | 5.76 | 5.76 | 2.88 | 2.88 | 5.76 | 5.76 | 2.88 | 2.88 |
| Citric acid (g) | 6.4 | 6.4 | 6.4 | 6.4 | 6.4 | 6.4 | 6.4 | 6.4 |
| Magnesium oxide (g) | 1.87 | 1.87 | 1.87 | 1.87 | 1.87 | 1.87 | 1.87 | 1.87 |
| $KHCO_3$ (g) | 0.267 | 0.267 | 0.267 | 0.267 | 0.267 | 0.267 | 0.267 | 0.267 |
| Na-saccharin (g) | 0.065 | 0.065 | 0.065 | 0.065 | 0.065 | 0.065 | 0.065 | 0.065 |
| Methyl paraben (g) | 0.08 | 0.08 | 0.08 | 0.08 | 0.08 | 0.08 | 0.08 | 0.08 |
| Propyl paraben (g) | 0.016 | 0.016 | 0.016 | 0.016 | 0.016 | 0.016 | 0.016 | 0.016 |
| Berry flavor (g) | 0.065 | 0.065 | 0.065 | 0.065 | | | | |
| Orange flavor (g) | | | | | 0.033 | 0.033 | 0.033 | 0.033 |
| EDTA (g) | 0.028 | 0.028 | 0.028 | 0.028 | 0.028 | 0.028 | 0.028 | 0.028 |
| HCl (12M) (mL) | 2.38 | 2.38 | 2.88 | 2.88 | 2.38 | 2.38 | 2.88 | 2.88 |
| NaOH (g) | 1.01 | 1.11 | 0.76 | 0.75 | 1.01 | 1.11 | 0.76 | 0.75 |
| Sodium picosulfate (g) | 0.0055 | 0.0055 | 0.0055 | 0.0055 | 0.0055 | 0.0055 | 0.0055 | 0.0055 |
| pH | 4.8 | 4.7 | 4.8 | 4.8 | 4.8 | 4.7 | 4.8 | 4.8 |
| Time to ppt (d) | 15 | 15 | 15 | 20 | 15 | 15 | 15 | 15 |

Examples 130-138

Sodium Carboxymethylcellulose Stabilized Sodium Picosulfate/Magnesium Citrate Formulations Solutions are prepared as follows:
1. Na-CMC (AQUALON® 7L2P), EDTA, methyl paraben and propyl paraben are dissolved in water with heating and the solution is then allowed to cool to ambient temperature.
2. Citric acid and magnesium oxide are added and dissolved by mixing.
3. Na-saccharin and flavor are added and dissolved.
4. The solutions are weighed, and any water lost is replaced.
5. The pH is adjusted to 4.5, 4.8 or 5.2 with HCl (12 M) and/or NaOH.
6. Sodium picosulfate is added.

The solutions are stored at 20° C. and observed periodically until precipitation from the solution is noted. The results for various formulations are shown in Table 14.

Examples 139-147

Sodium Carboxymethylcellulose and Sodium Acetate Stabilized Sodium Picosulfate/Magnesium Citrate Formulations Solutions are prepared as follows:
1. Na-CMC (AQUALON® 7L2P), EDTA, methyl paraben and propyl paraben are dissolved in water with heating and the solution is then allowed to cool to ambient temperature.
2. Sodium acetate trihydrate is added and the pH of the solution is adjusted to about 3 with HCl (12 M).
3. Citric acid and magnesium oxide are added and dissolved by mixing.
4. Na-saccharin and flavor are added and dissolved.
5. The solutions are weighed, and any water lost is replaced.
6. The pH is adjusted to 4.5, 4.8 or 5.2 with HCl (12 M) and/or NaOH.
7. Sodium picosulfate is added.

TABLE 14

Sodium Carboxymethylcellulose-Stabilized Sodium Picosulfate/Magnesium Citrate Formulations

| Example | 130 | 131 | 132 | 133 | 134 | 135 | 136 | 137 | 138 |
|---|---|---|---|---|---|---|---|---|---|
| Water (mL) | 80 | 80 | 80 | 80 | 80 | 80 | 80 | 80 | 80 |
| Na-CMC (AQUALON ® 7L2P) (g) | 0.361 | 0.361 | 0.361 | 0.722 | 0.722 | 0.722 | 1.444 | 1.444 | 1.444 |
| Citric acid (g) | 6.4 | 6.4 | 6.4 | 6.4 | 6.4 | 6.4 | 6.4 | 6.4 | 6.4 |
| Magnesium oxide (g) | 1.87 | 1.87 | 1.87 | 1.87 | 1.87 | 1.87 | 1.87 | 1.87 | 1.87 |
| Na-saccharin (g) | 0.064 | 0.064 | 0.064 | 0.064 | 0.064 | 0.064 | 0.064 | 0.064 | 0.064 |
| Methyl paraben (g) | 0.08 | 0.08 | 0.08 | 0.08 | 0.08 | 0.08 | 0.08 | 0.08 | 0.08 |
| Propyl paraben (g) | 0.016 | 0.016 | 0.016 | 0.016 | 0.016 | 0.016 | 0.016 | 0.016 | 0.016 |
| Berry flavor (g) | 0.064 | 0.064 | 0.064 | 0.064 | 0.064 | 0.064 | 0.064 | 0.064 | 0.064 |
| EDTA (g) | 0.028 | 0.028 | 0.028 | 0.028 | 0.028 | 0.028 | 0.028 | 0.028 | 0.028 |
| HCl (12M) (mL) | 0.00 | 0.00 | 0.03 | 0.00 | 0.00 | 0.00 | 0.00 | 0.00 | 0.03 |
| NaOH (g) | 0.08 | 0.26 | 0.38 | 0.08 | 0.25 | 0.35 | 0.05 | 0.23 | 0.35 |
| Sodium picosulfate (g) | 0.0055 | 0.0055 | 0.0055 | 0.0055 | 0.0055 | 0.0055 | 0.0055 | 0.0055 | 0.0055 |
| pH | 4.5 | 4.9 | 5.2 | 4.5 | 4.8 | 5.2 | 4.5 | 4.8 | 5.2 |
| Time to ppt (d) | 15 | 7 | 7 | 7 | 7 | 7 | 7 | 7 | 7 |

The solutions are stored at 20° C. and observed periodically until precipitation from the solution is noted. The results for various formulations are shown in Table 15.

TABLE 15

Sodium Carboxymethylcellulose and Sodium Acetate-Stabilized Sodium Picosulfate/Magnesium Citrate Formulations

| Example | 139 | 140 | 141 | 142 | 143 | 144 | 145 | 146 | 147 |
|---|---|---|---|---|---|---|---|---|---|
| Water (mL) | 80 | 80 | 80 | 80 | 80 | 80 | 80 | 80 | 80 |
| Na-CMC (AQUALON ® 7L2P) (g) | 0.361 | 0.361 | 0.361 | 0.722 | 0.722 | 0.722 | 1.444 | 1.444 | 1.444 |
| Sodium acetate trihydrate (g) | 7.98 | 7.98 | 7.98 | 7.98 | 7.98 | 7.98 | 7.98 | 7.98 | 7.98 |
| Citric acid (g) | 6.4 | 6.4 | 6.4 | 6.4 | 6.4 | 6.4 | 6.4 | 6.4 | 6.4 |
| Magnesium oxide (g) | 1.87 | 1.87 | 1.87 | 1.87 | 1.87 | 1.87 | 1.87 | 1.87 | 1.87 |
| Na-saccharin (g) | 0.064 | 0.064 | 0.064 | 0.064 | 0.064 | 0.064 | 0.064 | 0.064 | 0.064 |
| Methyl paraben (g) | 0.08 | 0.08 | 0.08 | 0.08 | 0.08 | 0.08 | 0.08 | 0.08 | 0.08 |
| Propyl paraben (g) | 0.016 | 0.016 | 0.016 | 0.016 | 0.016 | 0.016 | 0.016 | 0.016 | 0.016 |
| Berry flavor (g) | 0.064 | 0.064 | 0.064 | 0.064 | 0.064 | 0.064 | 0.064 | 0.064 | 0.064 |
| EDTA (g) | 0.028 | 0.028 | 0.028 | 0.028 | 0.028 | 0.028 | 0.028 | 0.028 | 0.028 |
| HCl (12M) (mL) | 4.44 | 4.44 | 4.44 | 4.44 | 4.44 | 4.44 | 4.44 | 4.44 | 4.44 |
| NaOH (g) | 1.01 | 1.67 | 2.31 | 1.03 | 1.69 | 2.05 | 1.06 | 0.16 | 0.21 |
| Sodium picosulfate (g) | 0.0055 | 0.0055 | 0.0055 | 0.0055 | 0.0055 | 0.0055 | 0.0055 | 0.0055 | 0.0055 |
| pH | 4.5 | 4.8 | 5.2 | 4.5 | 4.9 | 5.2 | 4.5 | 4.8 | 5.2 |
| Time to ppt (d) | 55 | 85 | 60 | 65 | 85 | 80 | 80 | 70 | 50 |

Examples 148-156

Sodium Carboxymethylcellulose and Sodium Gluconate Stabilized Sodium Picosulfate/Magnesium Citrate Formulations Solutions are prepared as follows:
1. Na-CMC (AQUALON® 7L2P), EDTA, methyl paraben and propyl paraben are dissolved in water with heating and the solution is then allowed to cool to ambient temperature.
2. Sodium gluconate is added and the pH of the solution is adjusted to below 2.5 with HCl (12 M).
3. Citric acid and magnesium oxide are added and dissolved by mixing.
4. Na-saccharin and flavor are added and dissolved.
5. The solutions are weighed, and any water lost is replaced.
6. The pH is adjusted to 4.5, 4.8 or 5.2 with HCl (12 M) and/or NaOH.
7. Sodium picosulfate is added.

The solutions are stored at 20° C. until precipitation from the solution is observed. The results for various formulations are shown in Table 16.

TABLE 16

Sodium Carboxymethylcellulose and Sodium Gluconate-Stabilized Sodium Picosulfate/Magnesium Citrate Formulations

| Example | 148 | 149 | 150 | 151 | 152 | 153 | 154 | 155 | 156 |
|---|---|---|---|---|---|---|---|---|---|
| Water (mL) | 80 | 80 | 80 | 80 | 80 | 80 | 80 | 80 | 80 |
| Na-CMC (AQUALON ® 7L2P) (g) | 0.361 | 0.361 | 0.361 | 0.722 | 0.722 | 0.722 | 1.444 | 1.444 | 1.444 |
| Sodium gluconate (g) | 1.71 | 1.71 | 1.71 | 1.71 | 1.71 | 1.71 | 1.71 | 1.71 | 1.71 |
| Citric acid (g) | 6.4 | 6.4 | 6.4 | 6.4 | 6.4 | 6.4 | 6.4 | 6.4 | 6.4 |
| Magnesium oxide (g) | 1.87 | 1.87 | 1.87 | 1.87 | 1.87 | 1.87 | 1.87 | 1.87 | 1.87 |
| Na-saccharin (g) | 0.064 | 0.064 | 0.064 | 0.064 | 0.064 | 0.064 | 0.064 | 0.064 | 0.064 |
| Methyl paraben (g) | 0.08 | 0.08 | 0.08 | 0.08 | 0.08 | 0.08 | 0.08 | 0.08 | 0.08 |
| Propyl paraben (g) | 0.016 | 0.016 | 0.016 | 0.016 | 0.016 | 0.016 | 0.016 | 0.016 | 0.016 |
| Berry flavor (g) | 0.064 | 0.064 | 0.064 | 0.064 | 0.064 | 0.064 | 0.064 | 0.064 | 0.064 |
| EDTA (g) | 0.028 | 0.028 | 0.028 | 0.028 | 0.028 | 0.028 | 0.028 | 0.028 | 0.028 |
| HCl (12M) (mL) | 2.69 | 3.06 | 4.22 | 1.67 | 1.67 | 1.73 | 2.00 | 2.00 | 2.17 |
| NaOH (g) | 1.19 | 1.68 | 2.33 | 0.89 | 1.10 | 1.33 | 0.85 | 1.05 | 1.30 |
| Sodium picosulfate (g) | 0.0055 | 0.0055 | 0.0055 | 0.0055 | 0.0055 | 0.0055 | 0.0055 | 0.0055 | 0.0055 |
| pH | 4.5 | 4.8 | 5.2 | 4.5 | 4.9 | 5.1 | 4.5 | 4.8 | 5.2 |
| Time to ppt (d) | 70 | 145 | 155 | 75 | 180 | 85 | 80 | 75 | 75 |

Examples 157-165

Sodium Carboxymethylcellulose and Sodium Lactate Stabilized Sodium Picosulfate/Magnesium Citrate Formulations Solutions are prepared as follows:

1. Na-CMC (AQUALON® 7L2P), EDTA, methyl paraben and propyl paraben are dissolved in water with heating and the solution is then allowed to cool to ambient temperature.
2. Lactic acid and sodium lactate are added and allowed to dissolve, and the pH of the solution is adjusted to about 3 with HCl (12 M).
3. Citric acid and magnesium oxide are added and dissolved by mixing.
4. Na-saccharin and flavor are added and dissolved.
5. The solutions are weighed, and any water lost is replaced.
6. The pH is adjusted to 4.5, 4.8 or 5.2 HCl with (12 M) and/or NaOH.
7. Sodium picosulfate is added.

The solutions are stored at 20° C. until precipitation from the solution is observed. The results for various formulations are shown in Table 17.

TABLE 17

Sodium Carboxymethylcellulose and Sodium Lactate-Stabilized Sodium Picosulfate/Magnesium Citrate Formulations

| Example | 157 | 158 | 159 | 160 | 161 | 162 | 163 | 164 | 165 |
|---|---|---|---|---|---|---|---|---|---|
| Water (mL) | 80 | 80 | 80 | 80 | 80 | 80 | 80 | 80 | 80 |
| Na-CMC (AQUALON ® 7L2P) (g) | 0.361 | 0.361 | 0.361 | 0.722 | 0.722 | 0.722 | 1.444 | 1.444 | 1.444 |
| Lactic acid (g) | 0.722 | 0.722 | 0.722 | 0.722 | 0.722 | 0.722 | 0.722 | 0.722 | 0.722 |
| Sodium lactate (g) | 1.71 | 1.71 | 1.71 | 1.71 | 1.71 | 1.71 | 1.71 | 1.71 | 1.71 |
| Citric acid (g) | 6.4 | 6.4 | 6.4 | 6.4 | 6.4 | 6.4 | 6.4 | 6.4 | 6.4 |
| Magnesium oxide (g) | 1.87 | 1.87 | 1.87 | 1.87 | 1.87 | 1.87 | 1.87 | 1.87 | 1.87 |
| Na-saccharin (g) | 0.064 | 0.064 | 0.064 | 0.064 | 0.064 | 0.064 | 0.064 | 0.064 | 0.064 |
| Methyl paraben (g) | 0.08 | 0.08 | 0.08 | 0.08 | 0.08 | 0.08 | 0.08 | 0.08 | 0.08 |
| Propyl paraben (g) | 0.016 | 0.016 | 0.016 | 0.016 | 0.016 | 0.016 | 0.016 | 0.016 | 0.016 |
| Berry flavor (g) | 0.064 | 0.064 | 0.064 | 0.064 | 0.064 | 0.064 | 0.064 | 0.064 | 0.064 |
| EDTA (g) | 0.028 | 0.028 | 0.028 | 0.028 | 0.028 | 0.028 | 0.028 | 0.028 | 0.028 |
| HCl (12M) (mL) | 1.03 | 1.03 | 1.42 | 1.11 | 1.48 | 1.28 | 1.43 | 2.34 |
| NaOH (g) | 0.82 | 0.93 | 0.95 | 0.73 | 0.97 | 1.29 | 0.85 | 3.40 | 4.82 |
| Sodium picosulfate (g) | 0.0055 | 0.0055 | 0.0055 | 0.0055 | 0.0055 | 0.0055 | 0.0055 | 0.0055 | 0.0055 |
| pH | 4.5 | 4.8 | 5.2 | 4.5 | 4.9 | 5.1 | 4.5 | 4.8 | 5.2 |
| Time to ppt (d) | 65 | 55 | 50 | 30 | 35 | 14 | 60 | 50 | 40 |

Examples 166-198

Combined Effect of Carboxylic Acids and Polymers in Inhibiting Precipitation of Sodium Picosulfate/Magnesium Citrate Formulations If a polymer is included in the formulation, the polymer (75-150 mg) is dissolved in water (150 mL) until a clear solution (containing the polymer at a concentration of 0.5-1% (w/v)) is formed. A sachet of PREPOPIK® sodium picosulfate/magnesium citrate granules (containing sodium picosulfate (10 mg), magnesium oxide (3.5 g), citric acid (12 g), KHCO$_3$ (0.65 g), Na-saccharin and orange flavoring) is added. A carboxylic acid (31-63 mmol) is added, and the pH is adjusted to the range 4.7-5.1 using aq. NaOH and aq. HCl solutions. The solution is filtered through a 0.22 μm PTFE filter under vacuum. The resulting solution is subjected to testing under the freeze-thaw conditions as described in Example 3.

The amount of precipitate measured after five freeze-thaw cycles for solutions containing various carboxylic acid/polymer combinations is shown in Table 18.

TABLE 18

Precipitation of PREPOPIK ® Oral Solution containing Carboxylic Acids and Polymers as Precipitation Inhibitors

| | Precipitation Inhibitor(s) | | | Precipitation after Freeze-Cycles (mm) | | | | |
|---|---|---|---|---|---|---|---|---|
| Ex. | Carboxylic acid | Amount (mmol) | Polymer | Amount | 1st Cycle | 2nd Cycle | 3rd Cycle | 4th Cycle | 5th Cycle |
| Ref. | — | — | — | — | 2 | 4.5 | 36.5 | 37.5 | 37.5 |
| 166 | Malic acid | 63 | — | — | 0 | 0 | 0 | 0 | 0 |

TABLE 18-continued

Precipitation of PREPOPIK ® Oral Solution containing
Carboxylic Acids and Polymers as Precipitation Inhibitors

| | Precipitation Inhibitor(s) | | | | Precipitation after Freeze-Cycles (mm) | | | | |
|---|---|---|---|---|---|---|---|---|---|
| Ex. | Carboxylic acid | Amount (mmol) | Polymer | Amount | 1st Cycle | 2nd Cycle | 3rd Cycle | 4th Cycle | 5th Cycle |
| 167 | Malic acid | 31 | — | — | 1.5 | 6 | 16.5 | 18 | 20 |
| 168 | Malonic acid | 63 | — | — | 0 | 0 | 0 | 0 | 0 |
| 169 | Malonic acid | 31 | — | — | 0 | 0.5 | 1 | 4 | 4 |
| 170 | Tartaric acid | 63 | — | — | 0 | 0 | 0 | 0 | 0 |
| 171 | Tartaric acid | 31 | — | — | 0 | 9.5 | 15.5 | 18.5 | 20 |
| 172 | Gluconic acid (sodium salt) | 63 | — | — | 0 | 0 | 1.75 | 5 | 9 |
| 173 | Succinic acid | 125 | — | — | 0 | 0 | 1.5 | 3 | 4 |
| 174 | Succinic acid | 63 | — | — | 0.5 | 8.5 | 15.5 | 19 | 22.5 |
| 175 | Malic acid | 31 | Sodium | 0.5% | 0 | 2 | 5.5 | 7.5 | 11.5 |
| 176 | Malonic acid | 31 | carboxymethyl- | 0.5% | 0 | 0 | 1.5 | 2.5 | 3.5 |
| 177 | Tartaric acid | 31 | cellulose | 0.5% | 0 | 2 | 2.5 | 4.5 | 10 |
| 178 | Gluconic acid (sodium salt) | 63 | (AQUALON ® CMC-7L2P) | 0.5% | 0 | 0 | 0 | 0.5 | 1.25 |
| 179 | Succinic acid | 63 | | 0.5% | 0 | 1.5 | 6 | 13 | 16.5 |
| 180 | — | — | | 0.5% | 7.8 | 26.3 | 29.0 | 29.8 | 30.0 |
| 181 | Malic acid | 31 | Sodium alginate | 0.5% | 0 | 0 | 0 | 0 | 1.5 |
| 182 | Malonic acid | 31 | (PROTANAL ® | 0.5% | 0 | 0 | 0 | 0 | 0 |
| 183 | Tartaric acid | 31 | CR 8133) | 0.5% | 0 | 0 | 0 | 0 | 0 |
| 184 | Gluconic acid (sodium salt) | 63 | | 0.5% | 0 | 0 | 0 | 0 | 0 |
| 185 | Succinic acid | 63 | | 0.5% | 0 | 0 | 0 | 0 | 0 |
| 186 | — | — | | 0.5% | 1.8 | 6.5 | 18.3 | 25.3 | 27.0 |
| 187 | Malic acid | 31 | Carrageenan | 1.0% | 0 | 0 | 0 | 1 | 2.5 |
| 188 | Malonic acid | 31 | (VISCARIN ® | 1.0% | 0 | 0 | 0 | 0 | 0 |
| 189 | Tartaric acid | 31 | GP 109 NF) | 1.0% | 0.0 | 0.0 | 0.3 | 0.6 | 2.0 |
| 190 | Gluconic acid (sodium salt) | 63 | | 1.0% | 0 | 0 | 0 | 0 | 0 |
| 191 | Succinic acid | 63 | | 1.0% | 0 | 0 | 1 | 3 | 4 |
| 192 | — | — | | 1.0% | 0 | 0 | 0 | 1 | 3 |
| 193 | Malic acid | 31 | Xanthan Gum | 0.5% | 0.0 | 0.0 | 0.3 | 1.5 | 2.5 |
| 194 | Malonic acid | 31 | (XANTURAL ® | 0.5% | 0 | 0 | 0 | 0 | 0 |
| 195 | Tartaric acid | 31 | 75) | 0.5% | 0 | 0 | 0 | 1 | 2 |
| 196 | Gluconic acid (sodium salt) | 63 | | 0.5% | 0 | 0 | 0 | 0 | 0 |
| 197 | Succinic acid | | | 0.5% | 0 | 0 | 3 | 4 | 5 |
| 198 | — | — | | 0.5% | 0 | 0 | 0 | 0 | 0 |

As shown by the data in Table 18, certain carboxylic acid/polymer combinations, showed a synergistic effect in which the precipitation-inhibitor effect of the carboxylic acid and polymer in combination was greater than the carboxylic acid and polymer separately. In particular, sodium carboxymethylcellulose demonstrated synergy with malic acid, malonic acid, tartaric acid, gluconic acid, and sodium alginate demonstrated synergy with malic acid, malonic acid, tartaric acid, gluconic acid, and succinic acid.

Examples 199-204

Ammonium Chloride, Sodium Carboxymethylcellulose and Sodium Acetate-Stabilized Sodium Picosulfate/Magnesium Citrate Formulations Solutions are prepared as follows:
1. EDTA, methyl paraben, propyl paraben and Na-CMC (AQUALON® 7L2P) (optional), are dissolved in water with heating and the solution is then allowed to cool to ambient temperature.
2. Sodium acetate trihydrate is added and allowed to dissolve, and the pH of the solution is adjusted to about 3 with HCl (12 M).
3. Citric acid and magnesium oxide are added and dissolved by mixing.
4. Ammonium chloride, Na-saccharin and flavor are added and dissolved.
5. The solutions are weighed, and any water lost is replaced.
6. The pH is adjusted to 4.5, 4.8 or 5.2 with HCl (12 M) and/or NaOH.
7. Sodium picosulfate is added.

The solutions are stored at 20° C. until precipitation from the solution is observed. The results for various formulations are shown in Table 19.

TABLE 19

Ammonium Chloride, Sodium Carboxymethylcellulose and Sodium Acetate-
Stabilized Sodium Picosulfate/Magnesium Citrate Formulations

| Example | 199 | 200 | 201 | 202 | 203 | 204 |
|---|---|---|---|---|---|---|
| Water (mL) | 80 | 80 | 80 | 80 | 80 | 80 |
| Na-CMC (AQUALON ® 7L2P) (g) | 0.00 | 0.00 | 0.00 | 0.722 | 0.722 | 0.722 |

TABLE 19-continued

Ammonium Chloride, Sodium Carboxymethylcellulose and Sodium Acetate-Stabilized Sodium Picosulfate/Magnesium Citrate Formulations

| Example | 199 | 200 | 201 | 202 | 203 | 204 |
|---|---|---|---|---|---|---|
| Sodium acetate (g) | 4.79 | 4.79 | 4.79 | 4.79 | 4.79 | 4.79 |
| Citric acid (g) | 6.4 | 6.4 | 6.4 | 6.4 | 6.4 | 6.4 |
| Magnesium oxide (g) | 1.87 | 1.87 | 1.87 | 1.87 | 1.87 | 1.87 |
| Na-saccharin (g) | 0.064 | 0.064 | 0.064 | 0.064 | 0.064 | 0.064 |
| Methyl paraben (g) | 0.08 | 0.08 | 0.08 | 0.08 | 0.08 | 0.08 |
| Propyl paraben (g) | 0.016 | 0.016 | 0.016 | 0.016 | 0.016 | 0.016 |
| Berry flavor (g) | 0.064 | 0.064 | 0.064 | 0.064 | 0.064 | 0.064 |
| $NH_4Cl$ (g) | 1.81 | 1.81 | 1.81 | 1.81 | 1.81 | 1.81 |
| EDTA (g) | 0.028 | 0.028 | 0.028 | 0.028 | 0.028 | 0.028 |
| HCl (12M) (mL) | 3.33 | 3.40 | 3.33 | 3.33 | 3.33 | 3.33 |
| NaOH (g) | 1.06 | 1.40 | 1.68 | 0.97 | 1.31 | 1.62 |
| Sodium picosulfate (g) | 0.0055 | 0.0055 | 0.0055 | 0.0055 | 0.0055 | 0.0055 |
| pH | 4.5 | 4.8 | 5.2 | 4.5 | 4.7 | 5.3 |
| Time to ppt (d) | 30 | 25 | 20 | 25 | 20 | 25 |

Examples 205-210

Ammonium Chloride, Sodium Carboxymethylcellulose and Sodium Gluconate-Stabilized Sodium Picosulfate/Magnesium Citrate Formulations Solutions are prepared as follows:
1. EDTA, methyl paraben, propyl paraben and Na-CMC (AQUALON® 7L2P) (optional), are dissolved in water with heating and the solution is then allowed to cool to ambient temperature.
2. Ammonium chloride, citric acid and magnesium oxide are added and dissolved by mixing.
3. Sodium gluconate is added and allowed to dissolve.
4. Na-saccharin and flavor are added and dissolved.
5. The solutions are weighed, and any water lost is replaced.
6. The pH is adjusted to 4.5, 4.8 or 5.2 with HCl (12 M) and/or NaOH.
7. Sodium picosulfate is added.

The solutions are stored at 20° C. until precipitation from the solution is observed. The results for various formulations are shown in Table 20.

Examples 211-216

Ammonium Chloride, Sodium Carboxymethylcellulose and Sodium Lactate-Stabilized Sodium Picosulfate/Magnesium Citrate Formulations Solutions are prepared as follows:
1. EDTA, methyl paraben, propyl paraben and Na-CMC (AQUALON® 7L2P) (optional), are dissolved in water with heating and the solution is then allowed to cool to ambient temperature.
2. Sodium acetate and lactic acid are added and allowed to dissolve, and the pH of the solution is adjusted to about 3 with HCl (12 M).
3. Citric acid and magnesium oxide are added and dissolved by mixing.
4. Ammonium chloride, Na-saccharin and flavor are added and dissolved.
5. The solutions are weighed, and any water lost is replaced.
6. The pH is adjusted to 4.5, 4.8 or 5.2 with HCl (12 M) and/or NaOH.
7. Sodium picosulfate is added.

TABLE 20

Ammonium Chloride, Sodium Carboxymethylcellulose and Sodium Gluconate-Stabilized Sodium Picosulfate/Magnesium Citrate Formulations

| Example | 205 | 206 | 207 | 208 | 209 | 210 |
|---|---|---|---|---|---|---|
| Water (mL) | 80 | 80 | 80 | 80 | 80 | 80 |
| Na-CMC (AQUALON ® 7L2P) (g) | 0.00 | 0.00 | 0.00 | 0.722 | 0.722 | 0.722 |
| Sodium gluconate (g) | 5.12 | 5.12 | 5.12 | 5.12 | 5.12 | 5.12 |
| Citric acid (g) | 6.4 | 6.4 | 6.4 | 6.4 | 6.4 | 6.4 |
| Magnesium oxide (g) | 1.87 | 1.87 | 1.87 | 1.87 | 1.87 | 1.87 |
| Na-saccharin (g) | 0.064 | 0.064 | 0.064 | 0.064 | 0.064 | 0.064 |
| Methyl paraben (g) | 0.08 | 0.08 | 0.08 | 0.08 | 0.08 | 0.08 |
| Propyl paraben (g) | 0.016 | 0.016 | 0.016 | 0.016 | 0.016 | 0.016 |
| Berry flavor (g) | 0.064 | 0.064 | 0.064 | 0.064 | 0.064 | 0.064 |
| $NH_4Cl$ (g) | 1.81 | 1.81 | 1.81 | 1.81 | 1.81 | 1.81 |
| EDTA (g) | 0.028 | 0.028 | 0.028 | 0.028 | 0.028 | 0.028 |
| HCl (12M) (mL) | 2.90 | 2.97 | 2.97 | 2.89 | 2.89 | 2.89 |
| NaOH (g) | 1.37 | 1.52 | 1.58 | 1.27 | 1.47 | 1.55 |
| Sodium picosulfate (g) | 0.0055 | 0.0055 | 0.0055 | 0.0055 | 0.0055 | 0.0055 |
| pH | 4.6 | 4.8 | 5.2 | 4.6 | 4.8 | 5.3 |
| Time to ppt (d) | 2 | 2 | 3 | 10 | 3 | 10 |

The solutions are stored at 20° C. until precipitation from the solution is observed. The results for various formulations are shown in Table 21.

TABLE 21

Ammonium Chloride, Sodium Carboxymethylcellulose and Sodium Lactate-Stabilized Sodium Picosulfate/Magnesium Citrate Formulations

| Example | 211 | 212 | 213 | 214 | 215 | 216 |
|---|---|---|---|---|---|---|
| Water (mL) | 80 | 80 | 80 | 80 | 80 | 80 |
| Na-CMC (AQUALON ® 7L2P) (g) | 0.00 | 0.00 | 0.00 | 0.722 | 0.722 | 0.722 |
| Sodium lactate (g) | 2.41 | 2.41 | 2.41 | 2.41 | 2.41 | 2.41 |
| Lactic acid (g) | 0.722 | 0.722 | 0.722 | 0.722 | 0.722 | 0.722 |
| Citric acid (g) | 6.4 | 6.4 | 6.4 | 6.4 | 6.4 | 6.4 |
| Magnesium oxide (g) | 1.87 | 1.87 | 1.87 | 1.87 | 1.87 | 1.87 |
| Na-saccharin (g) | 0.064 | 0.064 | 0.064 | 0.064 | 0.064 | 0.064 |
| Methyl paraben (g) | 0.08 | 0.08 | 0.08 | 0.08 | 0.08 | 0.08 |
| Propyl paraben (g) | 0.016 | 0.016 | 0.016 | 0.016 | 0.016 | 0.016 |
| Berry flavor (g) | 0.064 | 0.064 | 0.064 | 0.064 | 0.064 | 0.064 |
| $NH_4Cl$ (g) | 1.81 | 1.81 | 1.81 | 1.81 | 1.81 | 1.81 |
| EDTA (g) | 0.028 | 0.028 | 0.028 | 0.028 | 0.028 | 0.028 |
| HCl (12M) (mL) | 1.00 | 1.00 | 1.33 | 1.11 | 1.11 | 1.11 |
| NaOH (g) | 0.79 | 0.95 | 1.22 | 0.79 | 0.97 | 1.11 |
| Sodium picosulfate (g) | 0.0055 | 0.0055 | 0.0055 | 0.0055 | 0.0055 | 0.0055 |
| pH | 4.6 | 4.8 | 5.2 | 4.5 | 4.8 | 5.3 |
| Time to ppt (d) | 35 | 25 | 20 | 42 | 56 | 56 |

Examples 217-219

Ammonium Chloride and Sodium Carboxymethylcellulose-Stabilized Sodium Picosulfate/Magnesium Citrate Formulations Solutions are prepared as follows:
1. EDTA, methyl paraben, propyl paraben and Na-CMC (AQUALON® 7L2P), are dissolved in water with heating and the solution is then allowed to cool to ambient temperature.
2. Citric acid and magnesium oxide are added and dissolved by mixing.
3. Ammonium chloride, Na-saccharin and flavor are added and dissolved.
4. The solutions are weighed, and any water lost is replaced.
5. The pH is adjusted to 4.5, 4.8 or 5.2 with HCl (12 M) and/or NaOH.
6. Sodium picosulfate is added.

The solutions are stored at 20° C. until precipitation from the solution is observed. The results for various formulations are shown in Table 22.

TABLE 22

Ammonium Chloride, Sodium Carboxymethylcellulose and Sodium Acetate-Stabilized Sodium Picosulfate/Magnesium Citrate Formulations

| Example | 217 | 218 | 219 |
|---|---|---|---|
| Water (mL) | 80 | 80 | 80 |
| Na-CMC (AQUALON ® 7L2P) (g) | 0.722 | 0.722 | 0.722 |
| Citric acid (g) | 6.4 | 6.4 | 6.4 |
| Magnesium oxide (g) | 1.87 | 1.87 | 1.87 |
| Na-saccharin (g) | 0.064 | 0.064 | 0.064 |
| Methyl paraben (g) | 0.08 | 0.08 | 0.08 |
| Propyl paraben (g) | 0.016 | 0.016 | 0.016 |
| Berry flavor (g) | 0.064 | 0.064 | 0.064 |
| $NH_4Cl$ (g) | 1.81 | 1.81 | 1.81 |
| EDTA (g) | 0.028 | 0.028 | 0.028 |
| HCl (12M) (mL) | 0.00 | 0.00 | 0.33 |
| NaOH (g) | 0.11 | 0.25 | 0.53 |
| Sodium picosulfate (g) | 0.0055 | 0.0055 | 0.0055 |
| pH | 4.5 | 4.8 | 5.3 |
| Time to ppt (d) | 50 | 60 | 50 |

Examples 220-222

Sodium Acetate-Stabilized Sodium Picosulfate/Magnesium Citrate Formulations

Solutions are prepared as follows:
1. EDTA, methyl paraben, propyl paraben and Na-CMC (AQUALON® 7L2P), are dissolved in water with heating and the solution is then allowed to cool to ambient temperature.
2. Sodium acetate trihydrate is added and allowed to dissolve. The pH is adjusted to about 3 using HCl (12 M).
3. Citric acid and magnesium oxide are added and dissolved by mixing.
4. Na-saccharin and flavor are added and dissolved.
5. The solutions are weighed, and any water lost is replaced.
6. The pH is adjusted to 4.5, 4.8 or 5.2 with HCl (12 M) and/or NaOH.
7. Sodium picosulfate is added.

The solutions are stored at 20° C. until precipitation from the solution is observed. The results for various formulations are shown in Table 23.

TABLE 23

Sodium Acetate-Stabilized Sodium Picosulfate/Magnesium Citrate Formulations

| Example | 220 | 221 | 222 |
|---|---|---|---|
| Water (mL) | 80 | 80 | 80 |
| Sodium acetate trihydrate (g) | 7.98 | 7.98 | 7.98 |
| Citric acid (g) | 6.4 | 6.4 | 6.4 |
| Magnesium oxide (g) | 1.87 | 1.87 | 1.87 |
| Na-saccharin (g) | 0.064 | 0.064 | 0.064 |
| Methyl paraben (g) | 0.08 | 0.08 | 0.08 |
| Propyl paraben (g) | 0.016 | 0.016 | 0.016 |
| Berry flavor (g) | 0.064 | 0.064 | 0.064 |
| EDTA (g) | 0.028 | 0.028 | 0.028 |
| HCl (12M) (mL) | 4.44 | 4.84 | 4.61 |
| NaOH (g) | 0.97 | 1.67 | 1.97 |
| Sodium picosulfate (g) | 0.0055 | 0.0055 | 0.0055 |
| pH | 4.5 | 4.8 | 5.3 |
| Time to ppt (d) | 28 | 35 | 35 |

Example 223

Ammonium Chloride and Sodium Acetate-Stabilized Sodium Picosulfate/Magnesium Citrate Formulation The formulation is prepared as follows:

1. EDTA and sodium benzoate are dissolved in water (3000 mL) at ambient temperature.
2. Sodium acetate trihydrate is added and dissolved by mixing. The pH is adjusted to about 3 using HCl (12 M).
3. Citric acid and magnesium oxide are added and dissolved by mixing.
4. Na-saccharin, flavor and ammonium chloride are added and dissolved.
5. The pH is adjusted to 4.8 with NaOH.
6. The volume of the solution is adjusted to a final volume of 4270 mL using water.
7. Sodium picosulfate is added.
8. The solution is filtered and filled into bottles at a volume of 160 mL/bottle.

The solution is stored at 20° C. and observed periodically. Results are shown in Table 24.

TABLE 24

Ammonium Chloride/Sodium Acetate-Stabilized Sodium Picosulfate/Magnesium Citrate Formulations

| Example | 223 |
|---|---|
| Water (mL) | 4267 |
| EDTA (g) | 1.867 |
| Sodium benzoate | 2.400 |
| Sodium acetate trihydrate (g) | 442 |
| HCl (12M) (mL) | 250 |
| Citric acid (g) | 320 |
| Magnesium oxide (g) | 93.33 |
| Na-saccharin (g) | 10.667 |
| Berry flavor (g) | 3.200 |
| NH$_4$Cl (g) | 121.735 |
| NaOH (g) | 101 |
| Sodium picosulfate (g) | 0.267 |
| pH | 4.9 |
| Time to ppt (d) | 70 |

Example 224

Stabilized Sodium Picosulfate/Magnesium Citrate Formulation Containing Malonic Acid as a Precipitation Inhibitor A stabilized sodium picosulfate/magnesium citrate formulation containing malonic acid as a precipitation inhibitor may be prepared with the composition shown in Table 25.

TABLE 25

Composition of a Stabilized Sodium Picosulfate/Magnesium Citrate Formulation Containing Malonic Acid as a Precipitation Inhibitor

| Ingredients | Weight/Unit Dose (g) |
|---|---|
| Purified water | 150 |
| Disodium edetate (EDTA) | 0.07 |
| Sodium benzoate | 0.090 |
| Malonic acid | 6.5 |
| Citric acid, anhydrous | 12.00 |
| Magnesium oxide | 3.50 |
| Sucralose | 0.200 |
| Acesulfame potassium | 0.200 |
| Berry flavor | 0.120 |
| Sodium hydroxide (pellets) | 4.560 |
| Sodium picosulfate | 0.010 |
| pH | 4.9 |
| Time to precipitation | >203 d* |

*No precipitation observed after 203 days.

Example 225

Stabilized Sodium Picosulfate/Magnesium Citrate Formulation Containing Malonic Acid and Sodium Alginate as Precipitation Inhibitors A stabilized sodium picosulfate/magnesium citrate formulation containing malonic acid and sodium alginate as precipitation inhibitors may be prepared with the composition shown in Table 26.

TABLE 26

Composition of a Stabilized Sodium Picosulfate/Magnesium Citrate Formulation Containing Malonic Acid and Sodium Alginate as Precipitation Inhibitors

| Ingredients | Weight/Unit Dose (g) |
|---|---|
| Purified water | 150 |
| Disodium edetate (EDTA) | 0.07 |
| Sodium benzoate | 0.090 |
| Malonic acid | 3.25 |
| Sodium alginate (PROTANAL ® CR 8133) | 0.8 |
| Citric acid, anhydrous | 12.00 |
| Magnesium oxide | 3.50 |
| Sucralose | 0.200 |
| Acesulfame potassium | 0.200 |
| Berry flavor | 0.120 |
| Sodium hydroxide (pellets) | 4.560 |
| Sodium picosulfate | 0.010 |

OTHER EMBODIMENTS

It is to be understood that while the invention has been described in conjunction with the detailed description thereof, the foregoing description is intended to illustrate and not limit the scope of the invention, which is defined by the scope of the appended claims. A number of embodiments of the invention have been described. Nevertheless, it will be understood that various modifications may be made without departing from the spirit and scope of the invention. Accordingly, other aspects, advantages, embodiments and modifications are within the scope of the following claims.

What is claimed is:

1. A liquid pharmaceutical formulation comprising:
   (i) sodium picosulfate
   (ii) magnesium citrate; and
   (iii) malonic acid and at least one soluble anionic polymer as precipitation inhibitors;
   wherein the formulation is in the form of an aqueous solution having a pH in the range from about 4.0 to about 6.5.

2. A liquid pharmaceutical formulation comprising:
   (i) sodium picosulfate
   (ii) magnesium citrate; and
   (iii) malonic acid and sodium alginate as precipitation inhibitors;
   wherein the formulation is in the form of an aqueous solution having a pH in the range from about 4.0 to about 6.5.

3. A liquid pharmaceutical formulation comprising:
   sodium picosulfate;
   magnesium citrate; and
   malonic acid;
   wherein the formulation is in the form of an aqueous solution having a pH in the range from about 4.0 to about 6.5.

4. The liquid formulation of claim 3, wherein the malonic acid is present at a concentration in the range from about 0.1 M to about 1 M.

5. The liquid formulation of claim 1, wherein the sodium picosulfate is present at a concentration of from about 0.10 mM to about 0.15 mM, the formulation comprises magnesium and citrate in a molar ratio of from about 1:1 to about 1.5:1, and the magnesium is present at a concentration from about 0.2 M to about 0.8 M.

6. The liquid formulation of claim 1, wherein the sodium picosulfate is present at a concentration of from about 0.12 mM to about 0.14 mM, the formulation comprises magnesium and citrate in a molar ratio of about 1.4:1, and the magnesium is present at a concentration from about 0.5 to about 0.6 M.

7. The liquid formulation of claim 1, wherein the magnesium citrate is formed from magnesium oxide and citric acid.

8. The liquid formulation of claim 1, wherein the malonic acid is present at a concentration of from about 0.1 M to about 1 M.

9. The liquid formulation of claim 1, wherein the at least one soluble anionic polymer is selected from alginic acid, carboxymethylcellulose, carrageenans, polyacrylic acid and copolymers thereof, and xanthan gum.

10. The liquid formulation of claim 1, wherein the at least one soluble anionic polymer is alginic acid.

11. The liquid formulation of claim 1, wherein the at least one soluble anionic polymer is carboxymethylcellulose.

12. The liquid formulation of claim 1, wherein the at least one soluble anionic polymer is carrageenan or xanthan gum.

13. The liquid formulation of claim 1, wherein the at least one soluble anionic polymer is present at a concentration of from about 1 g/L to about 20 g/L.

14. The liquid formulation of claim 1, wherein the malonic acid is present at a concentration of from about 0.1 M to about 1 M, and the at least one soluble anionic polymer is present at a concentration of from about 1 g/L to about 20 g/L.

15. The liquid formulation of claim 2, wherein the sodium picosulfate is present at a concentration of from about 0.10 mM to about 0.15 mM, the formulation comprises magnesium and citrate in a molar ratio of from about 1:1 to about 1.5:1, and the magnesium is present at a concentration of from about 0.2 M to about 0.8 M.

16. The liquid formulation of claim 2, wherein the sodium picosulfate is present at a concentration of from about 0.12 mM to about 0.14 mM, the formulation comprises magnesium and citrate in a molar ratio of about 1.4:1, and the magnesium is present at a concentration of from about 0.5 to about 0.6 M.

17. The liquid formulation of claim 2, wherein the magnesium citrate is formed from magnesium oxide and citric acid.

18. The liquid formulation of claim 2, wherein the malonic acid is present at a concentration of from about 0.1 M to about 1 M.

19. The liquid formulation of claim 2, wherein the sodium alginate is present at a concentration of from about 1 g/L to about 20 g/L.

20. The liquid formulation of claim 2, wherein the malonic acid is present at a concentration of from about 0.1 M to about 1 M and the sodium alginate is present at a concentration of from about 1 g/L to about 20 g/L.

* * * * *